(12) United States Patent
Kawase et al.

(10) Patent No.: US 11,732,679 B2
(45) Date of Patent: Aug. 22, 2023

(54) FAILURE DIAGNOSTIC DEVICE FOR FUEL VAPOR PROCESSING APPARATUS

(71) Applicant: AISAN KOGYO KABUSHIKI KAISHA, Obu (JP)

(72) Inventors: Mariko Kawase, Funabashi (JP); Yuya Tanida, Obu (JP)

(73) Assignee: AISAN KOGYO KABUSHIKI KAISHA, Obu (JP)

( * ) Notice: Subject to any disclaimer, the term of this patent is extended or adjusted under 35 U.S.C. 154(b) by 0 days.

(21) Appl. No.: 17/725,332

(22) Filed: Apr. 20, 2022

(65) Prior Publication Data

US 2022/0341376 A1 Oct. 27, 2022

(30) Foreign Application Priority Data

Apr. 26, 2021 (JP) ................................. 2021-073882

(51) Int. Cl.
| | |
|---|---|
| *F02M 25/08* | (2006.01) |
| *G01N 33/28* | (2006.01) |
| *G01K 13/00* | (2021.01) |
| *G01N 9/26* | (2006.01) |
| *G01M 3/26* | (2006.01) |

(52) U.S. Cl.
CPC .... *F02M 25/0818* (2013.01); *F02M 25/0836* (2013.01); *F02M 25/0854* (2013.01); *G01K 13/00* (2013.01); *G01M 3/26* (2013.01); *G01N 9/26* (2013.01); *G01N 33/28* (2013.01); *F02M 2025/0845* (2013.01)

(58) Field of Classification Search
CPC .......... F02M 25/0809; F02M 25/0818; F02M 25/0836; F02M 2025/0845

USPC ....................... 73/114.39; 123/516, 518-521
See application file for complete search history.

(56) References Cited

U.S. PATENT DOCUMENTS

| | | | | |
|---|---|---|---|---|
| 6,148,803 | A * | 11/2000 | Majima | .............. F02M 25/0809 |
| | | | | 73/114.39 |
| 8,683,852 | B2 | 4/2014 | Makino | |
| 9,677,512 | B2 * | 6/2017 | Dudar | ................ F02M 25/0836 |
| 10,221,811 | B2 | 3/2019 | Kishi et al. | |
| 11,430,271 | B2 * | 8/2022 | Kishi | .................. F02M 25/0872 |
| 2002/0144667 | A1 * | 10/2002 | Ito | ............................ F02N 19/10 |
| | | | | 123/179.3 |

(Continued)

FOREIGN PATENT DOCUMENTS

| | | |
|---|---|---|
| JP | 2011157915 A | 8/2011 |
| JP | 5318793 B2 | 10/2013 |

*Primary Examiner* — Erick R Solis
(74) *Attorney, Agent, or Firm* — Conley Rose, P.C.

(57) ABSTRACT

A failure diagnostic device is configured to determine saturated vapor pressures of a fuel within a fuel tank. In a fuel vapor processing apparatus, some or all of the passages and spaces into which the fuel vapor flows into the fuel vapor processing apparatus are closed to the atmosphere. In this condition, the failure diagnostic device determines a plurality of saturated vapor pressure characteristics over time. The failure diagnostic device is configured to diagnose whether or not a leakage or a blockage failure in the fuel vapor processing apparatus is present. The failure diagnostic device determines a Reid vapor pressure (RVP) based on each of the plurality of determined saturated fuel vapor pressure characteristic and diagnoses whether or not a failure is present in accordance with a change in these RVPs over time.

9 Claims, 16 Drawing Sheets

(56) References Cited

U.S. PATENT DOCUMENTS

2005/0072221 A1* 4/2005 Itakura ............... F02M 25/0818
                                                    73/114.39
2020/0191098 A1* 6/2020 Kaneko .............. F02M 25/0818
2022/0389889 A1* 12/2022 Tanida ............... F02M 25/0818

* cited by examiner

FAILURE DIAGNOSTIC DEVICE FOR FUEL VAPOR PROCESSING APPARATUS

CROSS-REFERENCE TO RELATED APPLICATIONS

This application claims priority to Japanese patent application serial number 2021-073882 filed Apr. 26, 2021, the contents of which is hereby incorporated herein by reference in its entirety for all purposes.

BACKGROUND

Embodiments disclosed herein generally relate to failure diagnostic devices for fuel vapor processing apparatuses.

A fuel vapor processing apparatus serves to adsorb and capture fuel vapor in a canister, the fuel vapor having been generated within a fuel tank. The fuel vapor is released from the canister in a purging process, and is subsequently combusted, for example, in an engine. A failure diagnostic device may be provided to diagnose the airtightness of the fuel vapor processing apparatus or the blockage of venting lines.

One failure diagnostic device applies a positive pressure higher than atmospheric pressure or a negative pressure lower than atmospheric pressure into a diagnostic space where the failure diagnosis is to be performed. Changes in pressure in the diagnostic space before and after the start of the pressure application or changes in pressure in the diagnostic space after completion of the pressure application are detected. The failure diagnosis is performed for the airtightness of the diagnostic space and the blockage of venting lines based on changes in pressure of the diagnostic space.

SUMMARY

The above-described failure diagnostic device requires a pressure source to generate a positive pressure higher than atmospheric pressure or a negative pressure lower than atmospheric pressure in the diagnostic space. An energy source is also necessary for operating the pressure source.

Embodiments disclosed herein are for diagnosing failures of a fuel vapor processing apparatus based on changes in vapor pressures of the saturated fuel vapors within fuel tanks. Accordingly, such an approach to the failure diagnosis of fuel vapor processing apparatuses does not require a pressure source to generate a positive pressure higher than atmospheric pressure or a negative pressure lower than atmospheric pressure.

A fuel vapor processing apparatus according to one aspect of the present disclosure includes a canister configured to adsorb and capture fuel vapor generated within a fuel tank. A vapor passage is provided to the canister for introducing fuel vapor generate within the fuel tank to the canister. A vapor valve for opening and closing the vapor passage is provided. A purge passage is provided for allowing fuel vapor captured by the canister to flow therethrough for a purge treatment. A purge valve is provided for opening and closing the purge passage. An atmospheric passage is provided for supplying atmospheric air into the canister. An atmospheric valve is provided for opening and closing the atmospheric passage. A saturated vapor pressure characteristic estimating means (circuit) determines the saturated vapor pressure characteristics of the fuel within the fuel tank. A failure diagnosis means (circuit) performs diagnosis on whether or not a leakage failure of the fuel vapor processing apparatus or a blockage failure of the fuel vapor processing apparatus is present. The failure diagnosis means (circuit) performs diagnosis under the initial condition that all of the passages and spaces in the fuel vapor processing apparatus into which the fuel vapor flows are instructed to be closed to the atmosphere or under the condition that at least some of the passages or spaces in the fuel vapor processing apparatus into which the fuel vapor flows are open to the atmosphere. The saturated vapor pressure characteristic estimating means determines changes in the saturated vapor pressure characteristic over time. The failure diagnosis means determines the saturated vapor pressure at a specific temperature based on the saturated vapor pressure characteristic determined by the saturated vapor pressure characteristic estimating means. The failure diagnosis means diagnoses whether or not a failure is present based on a change in this saturated vapor pressure over time.

The device diagnoses a leakage failure of the fuel vapor processing apparatus assuming that the volatile components in the fuel are vaporized, despite being under a condition that they are not supposed to be. This diagnosis is performed when the saturated vapor pressure characteristic has changed under the condition in which all of the passages and spaces in the fuel vapor processing apparatus into which the fuel vapor flows are instructed to be closed to the atmosphere. Further, the fuel vapor processing apparatus diagnoses the blockage failure of the fuel vapor processing apparatus assuming that the volatile components have not vaporized, despite being under the condition that they are supposed to be. This diagnosis is performed when the saturated vapor pressure characteristic does not change under the condition in which at least some of the passages or the spaces into which the fuel vapor flows are open to the atmosphere. Therefore, the failure diagnosis of the fuel vapor processing apparatus can be performed without a pressure source to generate a positive pressure higher than the atmospheric pressure or a negative pressure lower than the atmospheric pressure. As a result, the energy required for operating the pressure source can be eliminated.

According to another aspect of the present disclosure, the saturated vapor pressure characteristic estimating means (circuit) includes a gas phase temperature detecting means (circuit) for detecting a temperature representing a headspace temperature of the fuel tank. Further, the saturated vapor pressure characteristic estimating means includes an aspirator that allows the fuel to flow through a narrow flow passage having a passage cross-sectional area narrower than that of an upstream side at a faster flow velocity, thereby generating a negative pressure in a decompression chamber near this narrow flow passage due to the Venturi effect. The saturated vapor pressure characteristic estimating means obtains a fuel vapor pressure determined by the pressure of the decompression chamber of the aspirator and the temperature detected by the gas phase temperature detecting means. The saturated vapor pressure characteristic estimating means estimates a saturated vapor pressure characteristic by comparing the fuel vapor pressure and the temperature with a stored saturated vapor pressure characteristic for that temperature.

The device can acquire the saturated fuel vapor pressure saturated in the decompression chamber of the aspirator. Therefore, the device can acquire the saturated vapor pressure characteristic based on its relationship with the gas phase temperature detected by the gas phase temperature detecting means.

According another aspect of the present disclosure, the saturated vapor pressure characteristic estimating means (circuit) includes a gas phase temperature detecting means (circuit) for detecting temperature representing the temperature of a head space of the fuel tank. Further, the saturated vapor pressure characteristic estimating means includes a vapor pressure detecting means (circuit) for determining a vapor pressure of the fuel vapor in the headspace of the fuel tank. The saturated vapor pressure characteristic estimating means obtains the vapor pressure detected by the vapor pressure detecting means before and after the change in temperature detected by the gas phase temperature detecting means. The saturated vapor pressure characteristic estimating means estimates the saturated vapor pressure characteristic by comparing the vapor pressure at each of these temperatures with saturated vapor pressures at these same temperature of the saturated vapor pressure characteristic that was stored in advance.

The device may estimate the saturated vapor characteristic only from the detected results of the gas phase temperature detecting means and the vapor pressure detecting means, thereby allowing the failure detection to be realized without using an aspirator, etc.

According to another aspect of the present disclosure, the saturated vapor pressure characteristic estimating means includes a gas phase temperature detecting means (circuit) for detecting the temperature of the headspace of the fuel tank. Further, the saturated vapor pressure characteristic estimating means includes a density detecting means (density detector) for detecting the density of the fuel component of the fuel vapor in the headspace of the fuel tank. The saturated vapor pressure characteristic estimating means obtains the fuel vapor pressure determined from the density of the fuel component of the fuel vapor detected by the density detecting means and the temperature detected by the gas phase temperature detecting means. The saturated vapor pressure characteristic estimating means estimates the saturated vapor pressure by comparing the fuel vapor pressure and the temperature with the stored saturated vapor pressure characteristic corresponding to this temperature.

The device may estimate the saturated vapor pressure characteristic using only the detected results of the gas phase temperature detecting means and the density detecting means.

According to another aspect of the present disclosure, the failure diagnosis means includes a first failure diagnosis means (circuit) to diagnoses whether or not a leakage failure is present in the fuel tank or the portion of the vapor passage on the fuel tank side of the vapor valve. The first failure diagnosis means diagnoses whether or not a leakage failure is present based on changes in the saturated vapor pressure in the headspace of the fuel tank over the course of time, the diagnosis being performed when the vapor valve is closed with the purge valve closed.

The device obtains changes in the saturated vapor pressure in the headspace within the fuel tank over time, with the fuel tank being closed to the atmosphere. The device may diagnose whether or not a leakage failure is present in the fuel tank or the passage leading to the tank based on changes in the saturated vapor pressure over time.

According to another aspect of the present disclosure, the failure diagnosis means (circuit) includes a second failure diagnosis means (circuit) to diagnose whether or not a leakage failure in at least one of the portion of the purge passages on the canister side, a blockage failure in the vapor passage including the vapor valve, or an opening operation failure of the vapor valve are present. The second failure diagnose means opens the vapor valve, closes the atmospheric valve, and closes the purge valve. This is done when the first failure diagnosis means determines "no leakage failure." The above-described diagnoses are performed on the canister, on the portion of the vapor passage on the canister side from the vapor valve, on the portion of the atmospheric passage on the canister side from the atmospheric valve, and on the portion of the purge passage on the canister side from the purge valve. These diagnoses are based on changes in the saturated vapor pressure in the headspace within the fuel tank over time.

The device can diagnose whether or not a leakage failure in the canister or the passage leading to the canister, a blockage failure in the vapor passage, or an opening operation failure of the vapor valve are present. These diagnoses are performed based on the change in the saturated vapor pressure in the headspace within the fuel tank over time. This diagnosis is performed while the fuel tank and the canister are in fluid communication with each other and blocked to the atmosphere. This diagnosis is performed after confirmation of no leakage failure as diagnosed by the first failure diagnosis means (circuit).

According to another aspect of the present disclosure, the failure diagnosis means includes a third failure diagnosis means (circuit) for diagnosing whether or not a blockage failure in the vapor passage, which includes the vapor valve, is present or whether or not an opening operation failure of the vapor valve is present. The third diagnosis means opens the vapor valve, opens the atmospheric valve, and closes the purge valve. The third diagnosis means performs the diagnosis when the first failure diagnosis means determines that no leakage failure was present. This diagnosis is performed in accordance with the change in the saturated vapor pressure in the headspace within the fuel tank over the course of time.

The device may diagnose whether or not a blockage failure in the vapor passage or an opening operation failure of the vapor valve is present. This diagnosis is performed in accordance with the change in the saturated vapor pressure in the headspace within the fuel tank over time. This diagnosis is performed when the fuel tank and the canister are in fluid communication with each other and in fluid communication with the atmosphere. This diagnosis is performed after confirmation of no leakage as diagnosed by the first failure diagnosis means (circuit).

According to another aspect of the present disclosure, the failure diagnosis means (circuit) includes a fourth failure diagnosis means (circuit) to diagnose whether or not a blockage failure in the atmospheric passage, which includes the atmospheric valve, or an opening operation failure of the atmospheric valve is present. The fourth failure diagnosis means opens the both vapor valve and atmospheric valve and closes the purge valve. This diagnosis is performed after the first failure diagnosis means and the second failure diagnosis means have determined that the leakage failure, the blockage failure, and/or the opening operation failure is/are absent. This diagnosis is performed in accordance with the change in the saturated vapor pressure in the headspace within the fuel tank over time.

The device may diagnose whether or not a blockage failure in the atmospheric passage is present. This diagnosis is performed in accordance with the change in the saturated vapor pressure in the headspace within the fuel tank over time. The diagnosis is performed while the fuel tank and the canister are in fluid communication with the atmosphere. This diagnosis is performed after confirmation of no leakage failure in the fuel tank or the canister. Further, at the same time, the device can diagnose whether or not an opening operation failure in the atmospheric valve is present.

According to another aspect of the present disclosure, the failure diagnosis means (circuit) includes a fifth failure diagnosis means (circuit) to diagnose whether or not a closing operation failure of the atmospheric valve is present. The fifth diagnosis means closes the atmospheric valve and closes the purge valve. This diagnosis is performed after the first failure diagnosis means and the third failure diagnosis means have determined that the leakage failure, the blockage failure, and/or the opening operation failure is/are absent. The diagnosis is performed in accordance with the change in the saturated vapor pressure in the headspace within the fuel tank over time.

The device may diagnose whether or not the closing operation failure of the atmospheric valve is present. This diagnosis is performed with the fuel tank and the canister in fluid communication with each other and opened to the atmosphere. This diagnosis is performed after the confirmation of no leakage failure, the blockage failure or the opening operation failure as diagnosed by the first failure diagnosis means and/or the third failure diagnosis means. This diagnosis is also performed in accordance with the change in the saturated vapor pressure in the headspace within the fuel tank over time. This diagnosis is performed while the atmospheric valve is closed.

DETAILED DESCRIPTION

Figure 1:
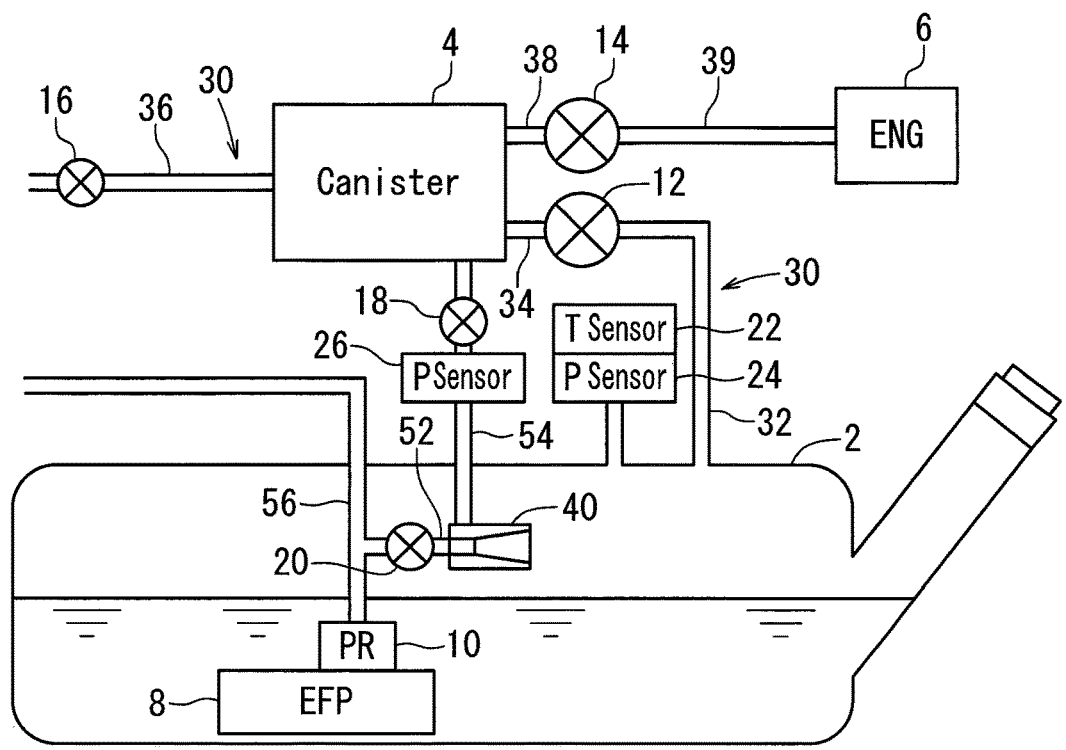
FIG. 1 is a schematic view of a first embodiment of a system in accordance with the principles described herein.

FIG. 1 shows a system configuration of a first embodiment of a failure diagnostic device for a fuel vapor processing apparatus. The first embodiment is an example of the failure diagnostic device applied to an engine, such as a gasoline engine or a diesel engine.

In FIG. 1, an upstream vapor passage 32 is connected to a fuel tank 2 and in fluid communication with a headspace of the fuel within the fuel tank 2. The fuel vapor, which is in the gas of the headspace, is adsorbed and captured by activated carbon (not shown) in a canister 4, which is coupled to and in selective fluid communication with the fuel tank 2 via the upstream vapor passage 32, a closing valve 12. (corresponding to a vapor valve), and a downstream vapor passage 34. One end of an atmospheric passage 36 is connected to the canister 4. The other end of the atmospheric passage 36 is open to the atmosphere via an atmospheric valve 16. When the fuel vapor pressure of the fuel gas in the fuel tank 2 exceeds the atmospheric pressure, the fuel vapor within the fuel tank 2 flows into the canister 4, and is adsorbed and captured by the canister 4 when the closing valve 12 and an atmospheric valve 16 are open.

As shown in FIG. 1, one end of an upstream purge passage 38 is connected to the canister 4 at a position adjacent the downstream vapor passage 34. The other end of the upstream purge passage 38 is in selective fluid communication with a downstream purge passage 39 via a purge valve 14. The other end of the downstream purge passage 39 is connected to an intake passage of an engine (ENG) 6. The engine 6 may be operated when the purge valve 14 and the atmospheric valve 16 are open. In this state, the fuel vapor captured in the canister 4 is directed into the engine 6 by the suction negative pressure of the engine 6. Accordingly, the captured fuel vapor is purged from the canister 4. The fuel vapor is then combusted in the engine 6. The fuel tank 2, the canister 4, the upstream vapor passage 32, the downstream vapor passage 34, the atmospheric passage 36, the upstream purge passage 38, and the downstream purge passage 39 are passages 30 (vapor passages) through which the fuel vapor may flow.

As shown in FIG. 1, a fuel pump (EFP) 8 is fixed at a bottom of the fuel tank 2 so as to be positioned within the liquid phase of the fuel within the fuel tank 2. The fuel within the fuel tank 2 can be supplied to the engine 6 via a fuel supply passage 56. A pressure regulator (PR) 10 is provided on the fuel pump 8. The pressure regulator 10 allows any quantify of fuel that is in excess of the fuel to be supplied to the engine 6 to flow back into the fuel tank 2. A branch passage 52 extends from the fuel supply passage 56. An intermediate branch valve 20 is disposed along the branch passage 52. The fuel is supplied to an aspirator (ASP) 40 via the branch passage 52. The aspirator 40 is fixed so as to be positioned in the portion of the fuel tank 2 where the fuel is in the gas phase, for example within the headspace of the fuel tank.

As shown in FIG. 1, the aspirator 40 generates a negative pressure in response to the fuel flowing therethrough. The generated negative pressure is applied to the canister 4, via a shutoff valve 18, through a suction passage 54. The suction passage 54 communicates with the canister 4 in a location adjacent to the downstream vapor passage 34 and the upstream purge passage 38. A pressure sensor (P sensor) 26 is provided along the suction passage 54 to detect the pressure within the suction passage 54. A temperature sensor (T sensor) 22 and a pressure sensor (P sensor) 24 are coupled to the fuel tank 2 and detect the temperature and pressure of the fuel in the gas phase, for example within the headspace of the fuel tank. The T sensor 22 and the P sensor 24 detect the temperature and the pressure, respectively, of the fuel vapor in the gas phase.

Figure 2:
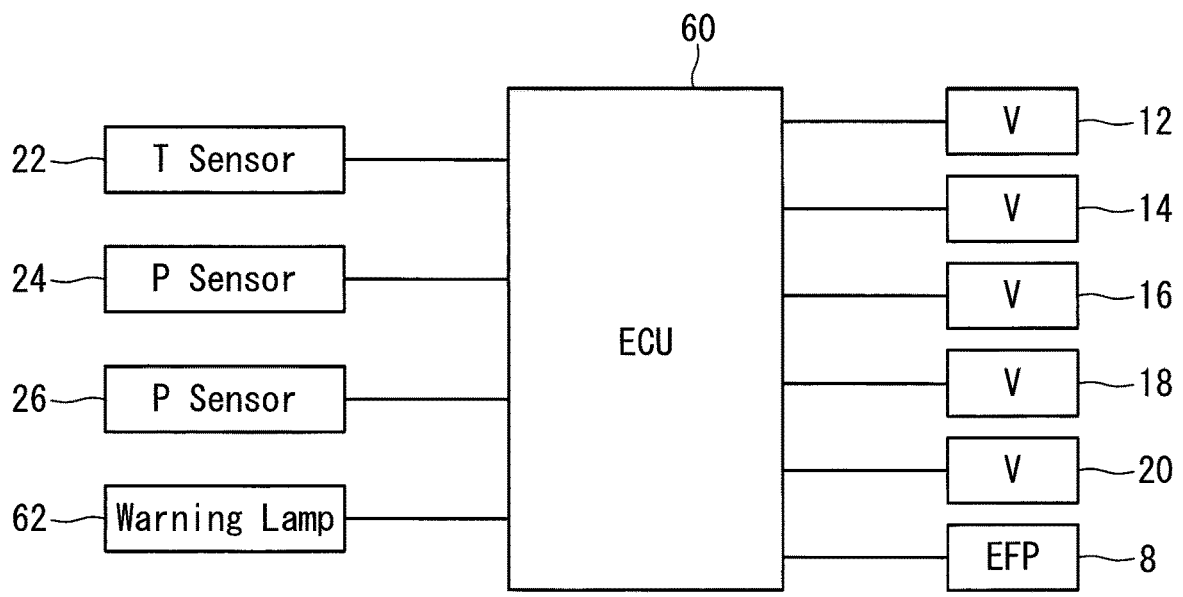
FIG. 2 is a block diagram of a control circuit of the system of FIG. 1.

FIG. 2 shows a control circuit for the system for the system shown in FIG. 1. In FIG. 2, detected signals from the temperature sensor 22 and the pressure sensors 24, 26 are communicated as inputs to a control unit 60, which may comprises a digital computer. The control unit 60 communicates and outputs activation signals to the closing valve 12, purge valve 14, atmospheric valve 16, shutoff valve 18, branch valve 20, and fuel pump 8 to control the operating conditions thereof. Further, the control unit 60 communicates and outputs activation signals to a warning lamp 62, as needed. The warning lamp 62 is illuminated when leakage of the vapor passage 30 to the atmosphere is detected by the leakage failure diagnosis, thereby warning a driver about the leakage.

Figure 3:
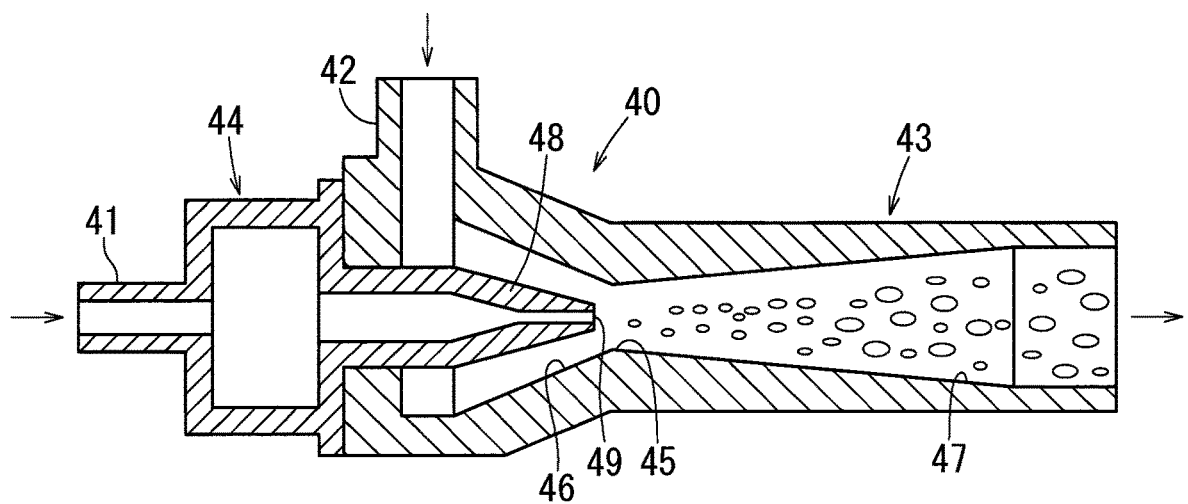
FIG. 3 is an enlarged cross-sectional view of the aspirator of FIG. 1.

As shown in FIG. 3, the aspirator 40 includes a venturi section 43 and a nozzle section 44. The fuel flows at relatively high speed from the nozzle section 44 to the venturi section 43. The fuel is injected from the venturi section 43 back into the fuel tank 2. The venturi section 43 includes a throat 45. A tapered decompression chamber 46 is provided on an upstream side of the throat 45 (relative to the direction of a fuel flow). A diffuser 47 that widens toward a downstream end is provided on a downstream side of the throat 45 (relative to the direction of a fuel flow). A suction port 42 is provided at the decompression chamber 46. The decompression chamber 46, the throat 45, and the diffuser 47 are coaxially aligned. The throat 45 forms a narrow flow passage having a cross-sectional area that is less than the upstream side and the downstream side (relative to the direction of a fuel flow).

As shown in FIG. 3, the suction port 42 is in fluid communication with the decompression chamber 46. The suction passage 54 (see FIG. 1) is in fluid communication with the suction port 42. The nozzle section 44 is attached to the upstream side of the venturi section 43. The nozzle section 44 includes an introduction port 41 for introducing fuel to the aspirator 40. The nozzle section 44 further includes a nozzle body 48 that injects the introduced fuel into the venturi section 43. The nozzle body 48 is coaxially disposed within the decompression chamber 46. The injection port 49 of the nozzle body 48 faces the throat 45.

As shown in FIG. 1, a portion of fuel discharged from the fuel pump 8 is introduced from the fuel supply passage 56 into the aspirator 40 via the branch passage 52. The fuel is introduced from the introduction port 41, shown in FIG. 3, to the aspirator 40. The fuel is injected by the nozzle body 48 and flows at relatively high speed in an axial direction through the center of the throat 45 and the diffuser 47. This generates a negative pressure in the decompression chamber 46 due to the venturi effect. This causes a suction force to be generated in the suction port 42 and the suction passage 54 (see FIG. 1). Gas is drawn to the suction port 42, via the suction passage 54. In the present, first embodiment, the gas is fuel vapor and air from the canister 4. The gas is mixed with the fuel injected from the nozzle body 48 and the mixture flows through the diffuser 47 and into the fuel tank 2.

Figure 4:
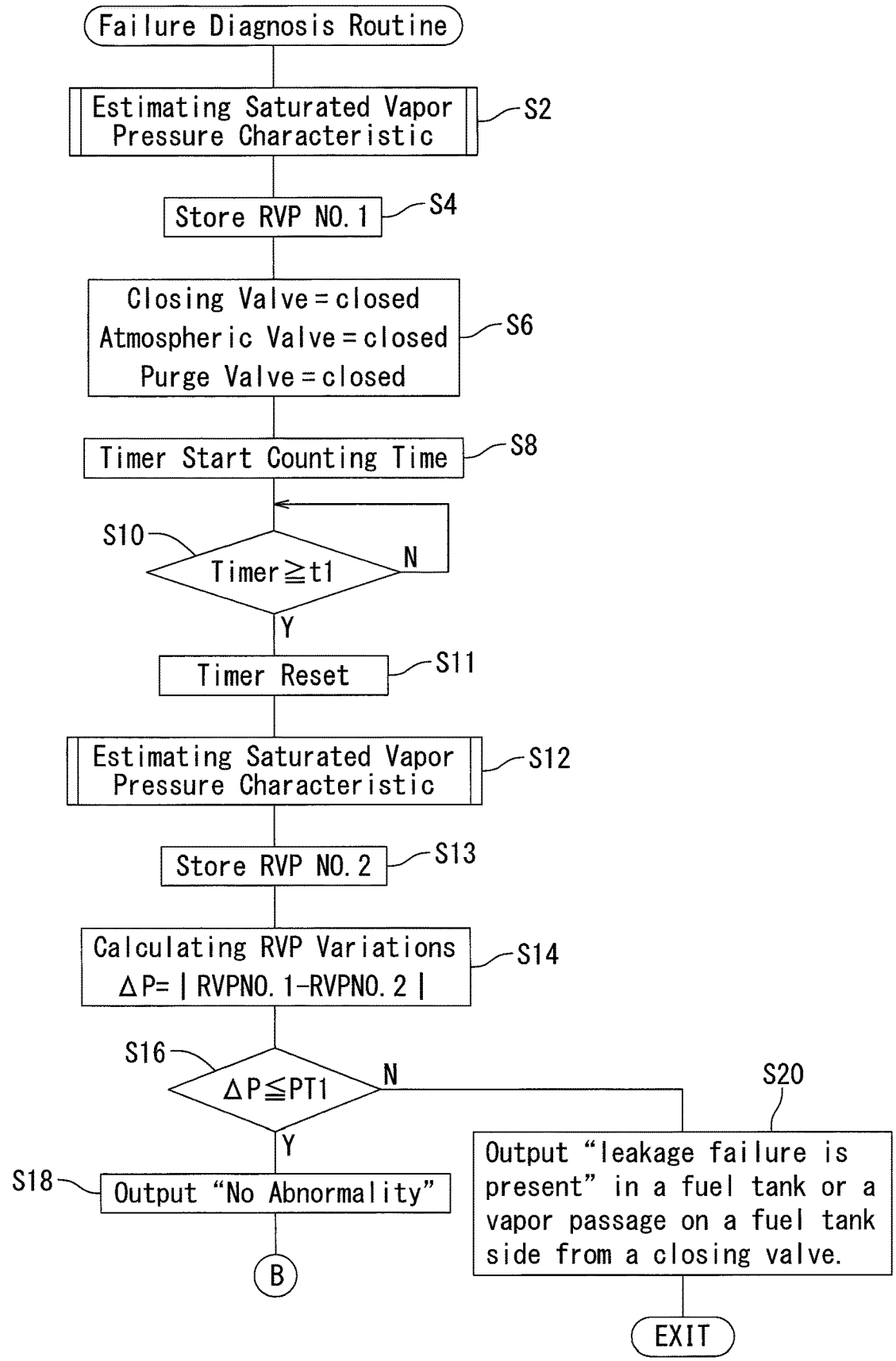
FIG. 4 is a flowchart illustrating a failure diagnosis program A for the system of FIG. 1.

FIG. 4 shows a program corresponding to a first failure diagnosis method or means for the above-described fuel vapor processing apparatus shown in FIG. 1. This program serves to diagnose and determine whether or not a leakage failure on the portion of the vapor passage 30 on the fuel tank side of the closing valve 12 or in the fuel tank 2 itself is present. Hereinafter, the contents of this program will be described with reference to a region representing Time A in the time chart of FIG. 10.

A program for a failure diagnosis routine A in FIG. 4 starts in a condition in which a temperature around the fuel tank 2 is stable and while the engine 6 is stopped. For example, the program may be started five hours after the engine has stopped. In Step S2, the saturated vapor pressure characteristics of the gas phase of the fuel in the fuel tank 2 are estimated, as will be described later. In Step S4, a Reid vapor pressure (RVP) at a gas phase temperature of 37.8° C. is determined based on the estimated saturated vapor pressure characteristics and is stored as RVP NO. 1. In Step S6, the closing valve 12, atmospheric valve 16, and purge valve 14 are all closed. Subsequently, in Step S8, a timer function is activated to start counting time. In Step S10, it is determined whether or not the time counted by the timer has reached a predetermined time t1. The time t1 is the time corresponding to a time A in FIG. 10. The system continues to wait until the counted time reaches t1. At such time, the timer function will be reset for a subsequent counting in Step S11.

As shown in FIG. 4, in a subsequent Step S12, the saturated vapor pressure characteristics of the gas phase of the fuel in the fuel tank 2 at such a moment are estimated again, similar to the above-described Step S2. In Step S13, similar to the above-described Step S4, the Reid vapor pressure (RVP) at a gas phase temperature of 37.8° C. is determined based on the current estimated saturated vapor pressure characteristics and stored as RVP NO. 2. In a following Step S14, the absolute value of the difference between RVP NO. 1 and RVP NO. 2 is determined and set as RVP variation $\Delta P$.

As shown in FIG. 4, in Step S16, it is determined whether or not the RVP variation $\Delta P$ is less than or equal to a first threshold value PT1. If a hole develops or has been opened in the fuel tank 2 and/or the portion of the vapor passage 30 on the fuel tank 2 side of the closing valve 12, a fuel vapor leakage may occur. For example, when a hole forms in the fuel tank 2 or the upstream vapor passage 32, which is on the side of the closing valve 12 having the fuel tank 2, a leakage of fuel vapor will occur. If a leakage of the fuel vapor is occurring, the Reid vapor pressure in the fuel tank 2 will become lower over time, as indicated by a broken line in the region for time A in FIG. 10. In such a case, Step S16 is determined to be negative, which results in an output of "leak failure is present" in Step S20. The warning lamp (see FIG. 2) is then illuminated. The failure diagnosis process will end for a while after the above-described output of the "leak failure is present" was performed. On the other hand, if there is no leakage failure, the Reid vapor pressure of the fuel tank 2 will not be lowered more than the threshold value, as indicated by a solid line in the region for time A in FIG. 10. Accordingly, Step S16 is determined to be positive and "No Abnormality" will be output in Step S18. The program then shifts to the program to execute the failure diagnosis illustrated in a region for time B in FIG. 10.

Figure 5:
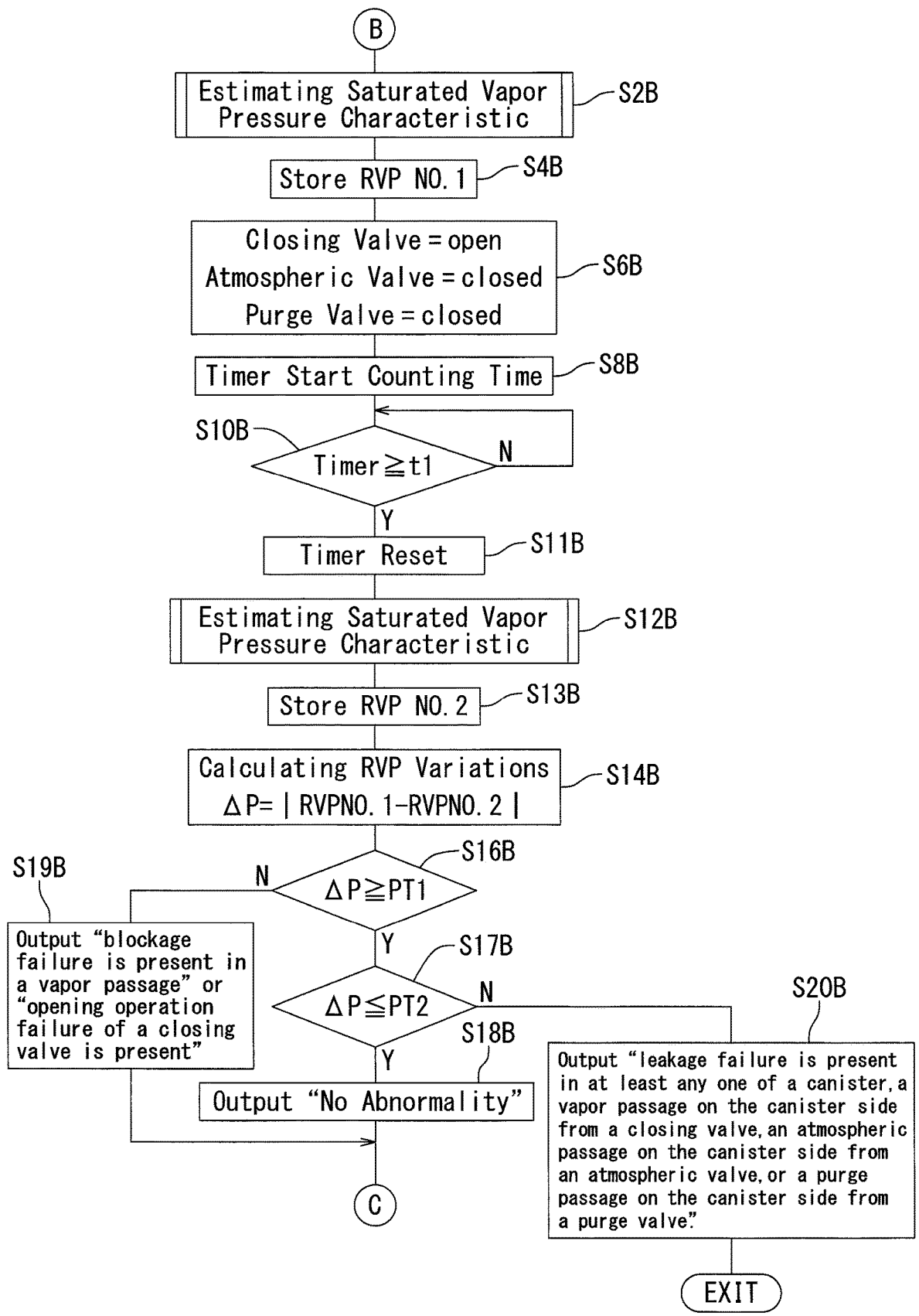
FIG. 5 is a flowchart illustrating a failure diagnosis program B for the system of FIG. 1.

FIG. 5 shows a program corresponding to a second failure diagnosis method or means for the above-described fuel vapor processing apparatus shown in FIG. 1. This program serves to diagnose whether or not a leakage failure is present in the portion of the vapor passage 30 on the canister 4 side of closing valve 12. Hereinafter, the contents of this program will be described with reference to the region representing time B in a time chart of FIG. 10.

When the program of FIG. 5 is executed, the saturated vapor pressure characteristics of the gas phase of the fuel in the fuel tank 2 at that moment are estimated in Step S2B in a similar manner as it was determined in Step S2 of the program in FIG. 4. In Step S4B, the Reid vapor pressure (RVP) at a gas phase temperature of 37.8° C. is determined based on the estimated saturated vapor pressure characteristics and stored as RVP NO. 1. In Step S6B, the atmospheric valve 16 and the purge valve 14 are maintained in the closed position, while the closing valve 12 is opened. Subsequently, in Step S8B to Step S13B, the Reid vapor pressure RVP NO. 2 is determined after a time t1 has elapsed and its value stored. In Step S14B, the absolute value of the difference between RVP NO. 1 and RVP NO. 2 is determined and set as RVP variation $\Delta P$ in a similar manner as it was done in Step S8 to Step S14 in FIG. 4.

As shown in FIG. 5, in the following Step S16B, it is determined whether or not the RVP variation $\Delta P$ is greater than or equal to the first threshold value PT1. Further, in Step S17B, it is determined whether or not the RVP variation $\Delta P$ is less than or equal to a second threshold value PT2. If there is a blockage failure in the vapor passage 30 on the canister 4 side of closing valve 12 or there is an opening operation failure of the closing valve 12, volatile components in fuel may not flow from the fuel tank 2 through the upstream vapor passage 32 and the downstream vapor passage 34 toward the canister 4. Therefore, as indicated by a dot-chain line in the region for time B of FIG. 10, the Reid vapor pressure would not be lowered below the threshold value PT1, even after the time B has elapsed. In such a situation, Step S16B is determined as negative, in Step S19B, the system outputs "blockage failure is present in the vapor passage" or "opening operation failure of the closing valve is present." The warning lamp 62 (see FIG. 2) is also illuminated.

When there is no blockage failure in the vapor passage 34 and there is no opening operation failure of the closing valve 12, the volatile components in the fuel in the fuel tank 2 flow toward the canister 4. Therefore, as indicated by a solid line in the region for time B in FIG. 10, the Reid vapor pressure is lowered. This results in the RVP variation $\Delta P$ being greater than or equal to the threshold value PT1. Accordingly, Step S16B is determined as affirmative.

On the other hand, a leakage failure may occur if there is a hole in at least one of the portion of the downstream vapor passage 34 on the canister 4 side of the closing valve 12, the portion of the atmospheric passage 36 on the canister 4 side of the atmospheric valve 16, or the portion of the upstream purge passage 38 on the canister 4 side of the purge valve 14. In this case, as indicated by a broken line in the region for time B in FIG. 10, the Reid vapor pressure is significantly lowered as compared to the case indicated by the solid line described above. Therefore, the RVP variation $\Delta P$ will be greater than or equal to the second threshold value PT2, and accordingly Step S17B will be determined as negative. Thus, in Step S20B, the system outputs a notification that there is a leakage failure in the canister 4 or in the vicinity of the canister 4. The vicinity of canister 4 may be, for example, the portion of the downstream vapor passage 34 on the canister 4 side of the closing valve 12, the portion of the atmospheric passage 36 on the canister 4 side of the atmospheric valve 16, or the portion of the upstream purge passage 38 on the canister 4 side of the purge valve 14. If there is a leakage failure, the warning lamp 62 is also illuminated (see FIG. 2). The failure diagnosis process will end for a while after the output of "leakage failure is present" is performed in this way.

Figure 10:
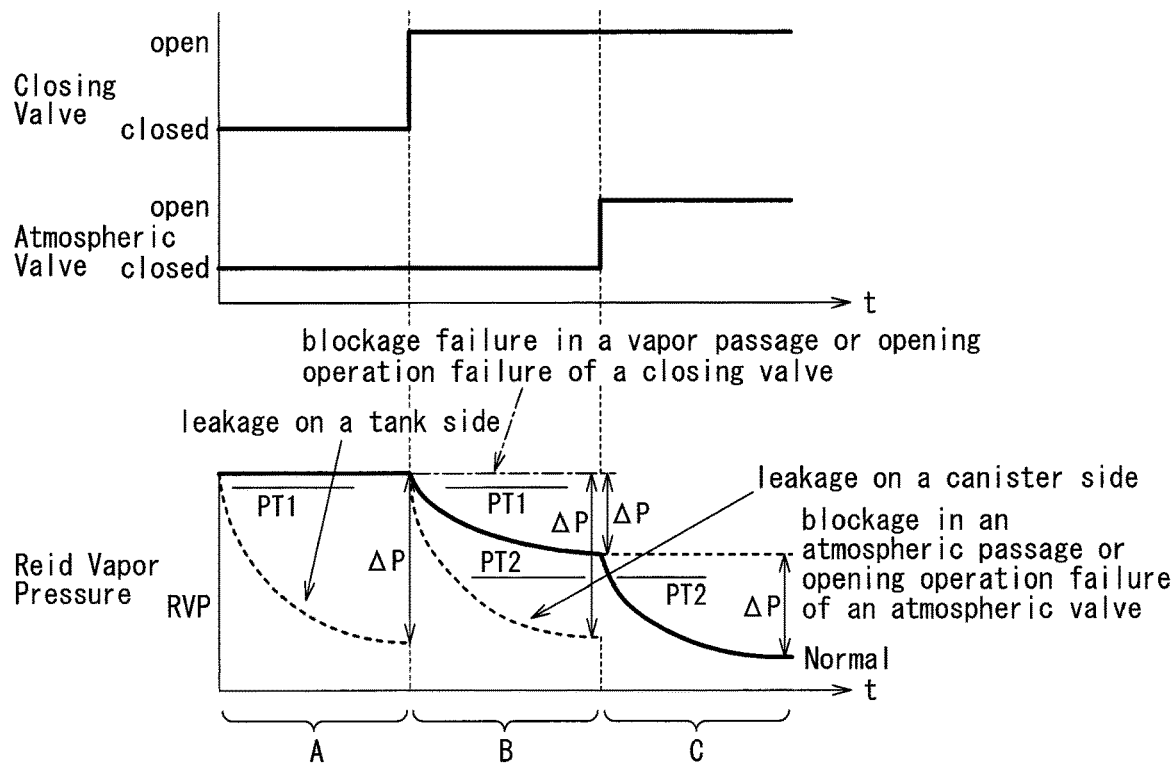
FIG. 10 is a time chart illustrating each of the failure diagnosis programs A to C.

If such a leakage failure in canister 4 as described-above is absent, the Reid vapor pressure may change as indicated by the solid line in the region for time B in FIG. 10. For instance, the Reid vapor pressure may change such that the RVP variation $\Delta P$ will be less than or equal to the second threshold value PT2. Therefore, Step S17B is determined to be affirmative and the system outputs "No Abnormality" in Step S18B. The program then shifts to the program to execute the failure diagnosis illustrated in a region for time C in FIG. 10.

Figure 6:
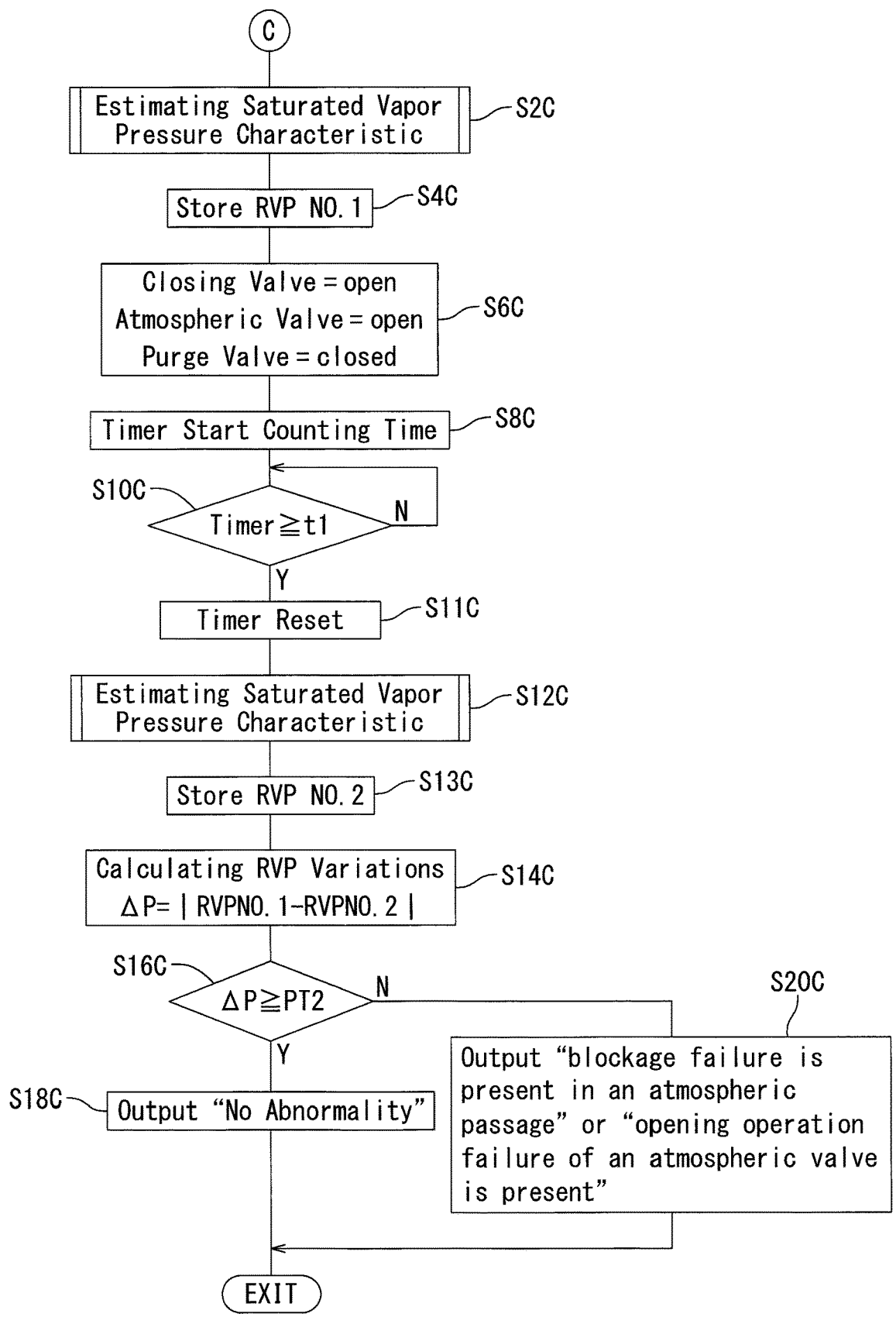
FIG. 6 is a flowchart illustrating a failure diagnosis program C for the system of FIG. 1.

FIG. 6 shows a program corresponding to a fourth failure diagnosis method or means for the above-described fuel vapor processing apparatus shown in FIG. 1. This program serves to diagnose whether or not a blockage failure is present in the atmospheric passage 36 of the vapor passage 30. Hereinafter, the contents of this program will be described with reference to a region representing time C in the time chart of FIG. 10.

When the program of FIG. 6 is executed, the saturated vapor pressure characteristics of the gas phase of the fuel in the fuel tank 2 at that moment will be estimated in Step S2C in a similar manner as was done in Step S2 of the program in FIG. 4. In Step S4C, the Reid vapor pressure (RVP) at a gas phase temperature of 37.8° C. is determined based on the estimated saturated vapor pressure characteristics and its value is stored as RVP NO. 1. In Step S6C, the closing valve 12 remains open, the purge valve 14 remains closed, and the atmospheric valve 16 is opened. Subsequently, in Step S8C to Step S13C, the Reid vapor pressure RVP NO. 2 is determined after a time t1 has elapsed and its value is stored. In Step S14C, the absolute value of the difference between RVP NO. 1 and RVP NO. 2 is determined and is set as the RVP variation $\Delta P$ in a similar manner as was done in Step S8 to Step S14 in FIG. 4.

In Step S16C, it is determined whether or not the RVP variation $\Delta P$ is greater than or equal to the second threshold value PT2. If there is a blockage failure in the atmospheric passage 36 or an opening operation failure of the closing valve 12, the Reid vapor pressure in the fuel tank 2 may be maintained in a condition higher than the second threshold PT2, as indicated by a broken line in the region for time C in FIG. 10, even after the time C has elapsed. Therefore, in such a situation, Step S16C is determined to be negative, and in Step S20C, the system outputs "blockage failure is present in the vapor passage" or "opening operation failure of the atmospheric valve is present." The warning lamp 62 (see FIG. 2) is also illuminated. In contrast, if there is no such a failure, the Reid vapor pressure in the fuel tank 2 is lowered, as indicated by a solid line in the region for time C in FIG. 10. Therefore, Step S16C is determined to be affirmative and the system outputs "No Abnormality" in Step S18C. Thereafter, this process of the failure diagnosis will end.

Figure 7:
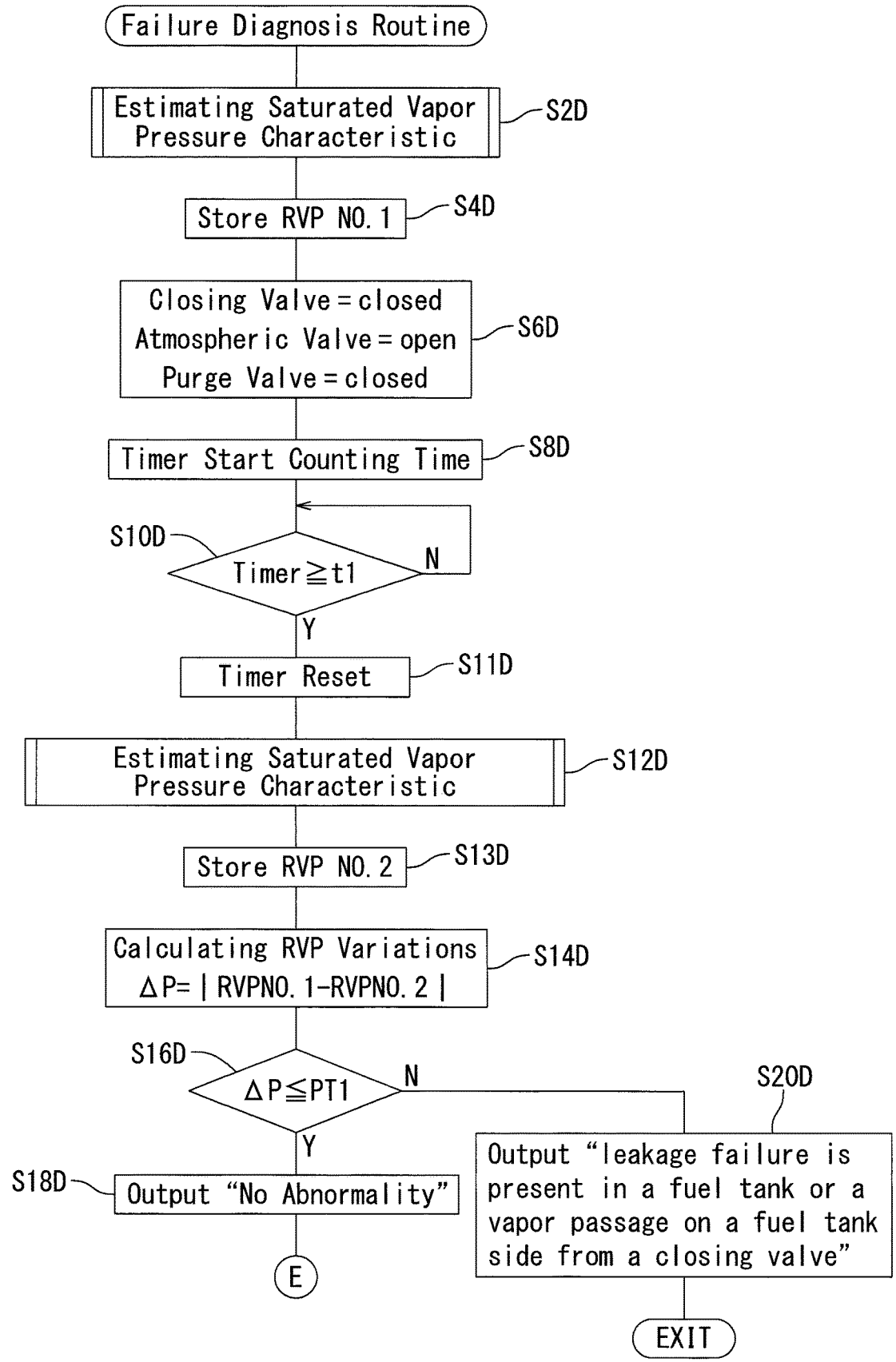
FIG. 7 is a flowchart illustrating a failure diagnosis program D for the system of FIG. 1.
Figure 11:
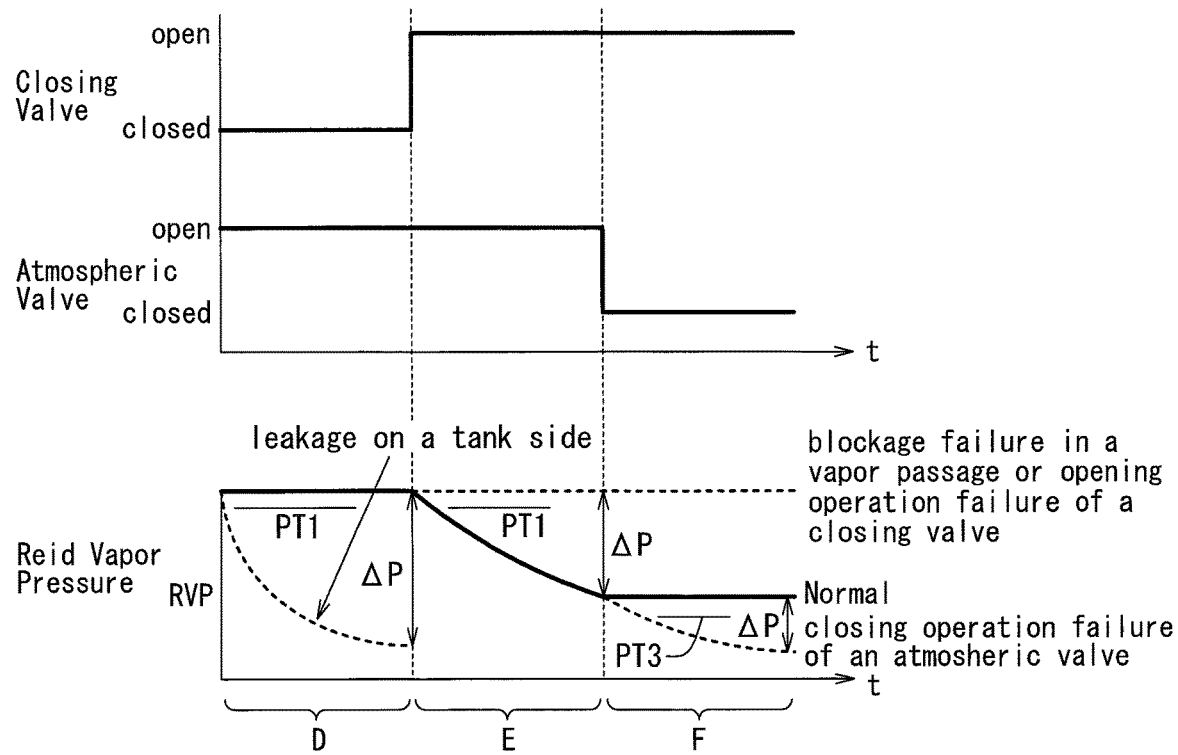
FIG. 11 is a time chart illustrating each of the failure diagnosis programs D to F.

FIG. 7 shows a program corresponding to a first failure diagnostic method or means for the above-described fuel vapor processing apparatus shown in FIG. 1. This program serves to diagnose whether or not a leakage failure on the fuel tank 2 or on a portion of the vapor passage 30 on the fuel tank 2 side of the closing valve 12 is present. This program is substantially the same as the program previously described and shown in FIG. 4. The primary difference between the program in FIG. 7 and the program in FIG. 4 is whether the atmospheric valve 16 is open or closed during the failure diagnosis. In the program of FIG. 7, the atmospheric valve 16 is open. However, whether or not the atmospheric valve 16 is open or closed will not substantially affect the diagnosis when the leakage failure diagnosis of the fuel tank 2 and the portion of the vapor passage 30 on the side of the fuel tank 2 of the closing valve 12 is performed while the closing valve 12 closed. Therefore, as is apparent from the similarities between the region for time A in FIG. 10 and the region for time D in FIG. 11, and since the program contents in FIG. 7 are substantially the same as the program contents in FIG. 4, the program contents in FIG. 7 will not be described in detail to avoid the repetition of the description of FIG. 4.

Figure 8:
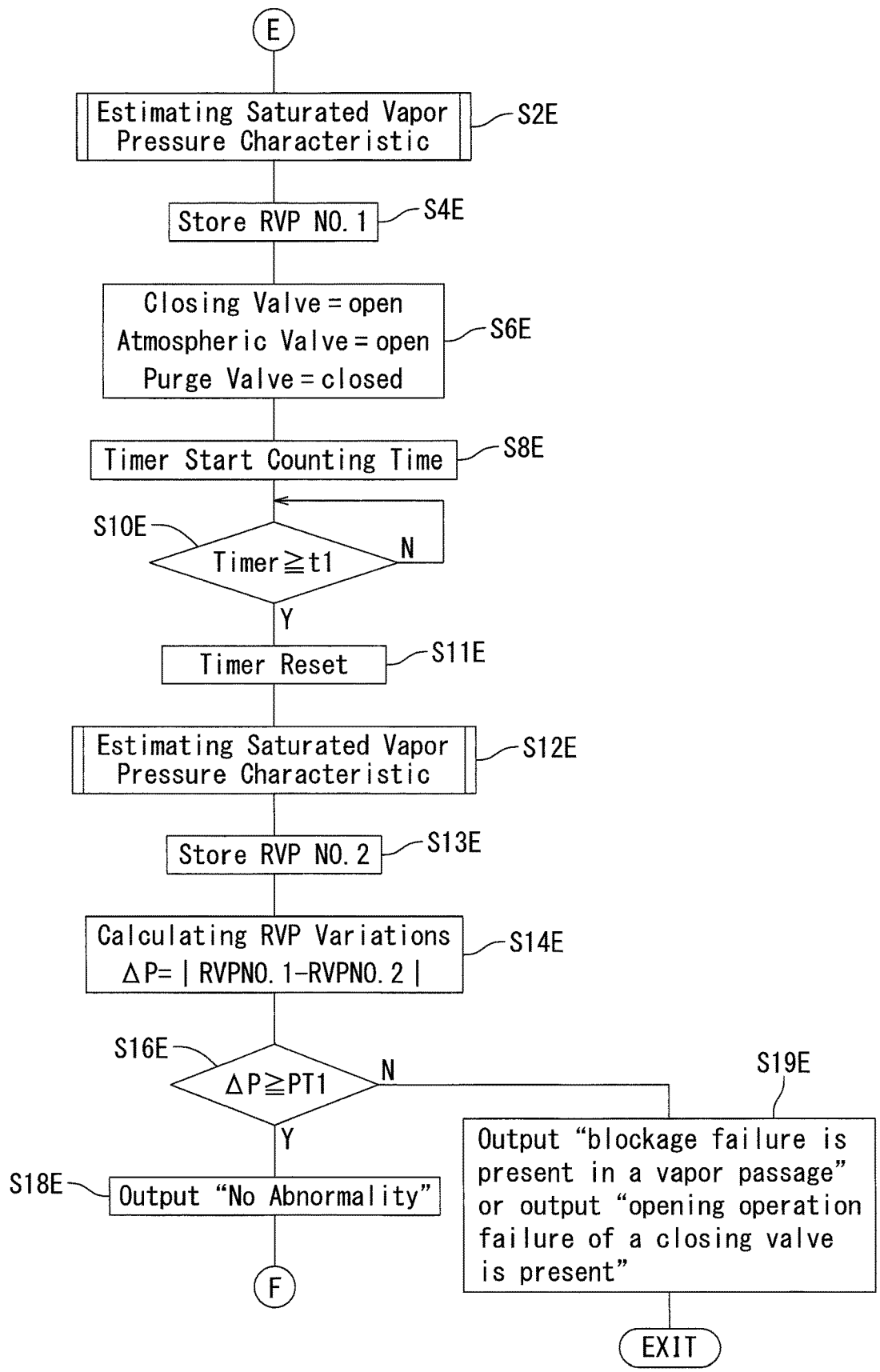
FIG. 8 is a flowchart illustrating a failure diagnosis program E for the system of FIG. 1.

In FIG. 8, a vapor passage failure is diagnosed for the above-described fuel vapor processing apparatus shown in FIG. 1. The vapor passage failure may be, for example, when the upstream vapor passage 32 and/or the downstream vapor passage 34 are blocked and/or there is an opening operation failure of the closing valve 12. This program is substantially the same as the program previously described and shown in FIG. 5. The main difference between the program in FIG. 8 and the program in FIG. 5 is whether the atmospheric valve 16 is open or closed during the failure diagnosis. However, whether or not the atmospheric valve 16 is open or closed does not affect the diagnosis when it is diagnosed whether there is this type of failure in the vapor passage. Therefore, as is apparent from the similarities between the region for time B in FIG. 10 and the region for time E in FIG. 11, and since the program contents in FIG. 8 are substantially the same as the program contents in FIG. 5 regarding diagnosis of this type of vapor passage failure, the program contents in FIG. 8 will not be described in detail to avoid the repetition of the description of FIG. 5.

Figure 9:
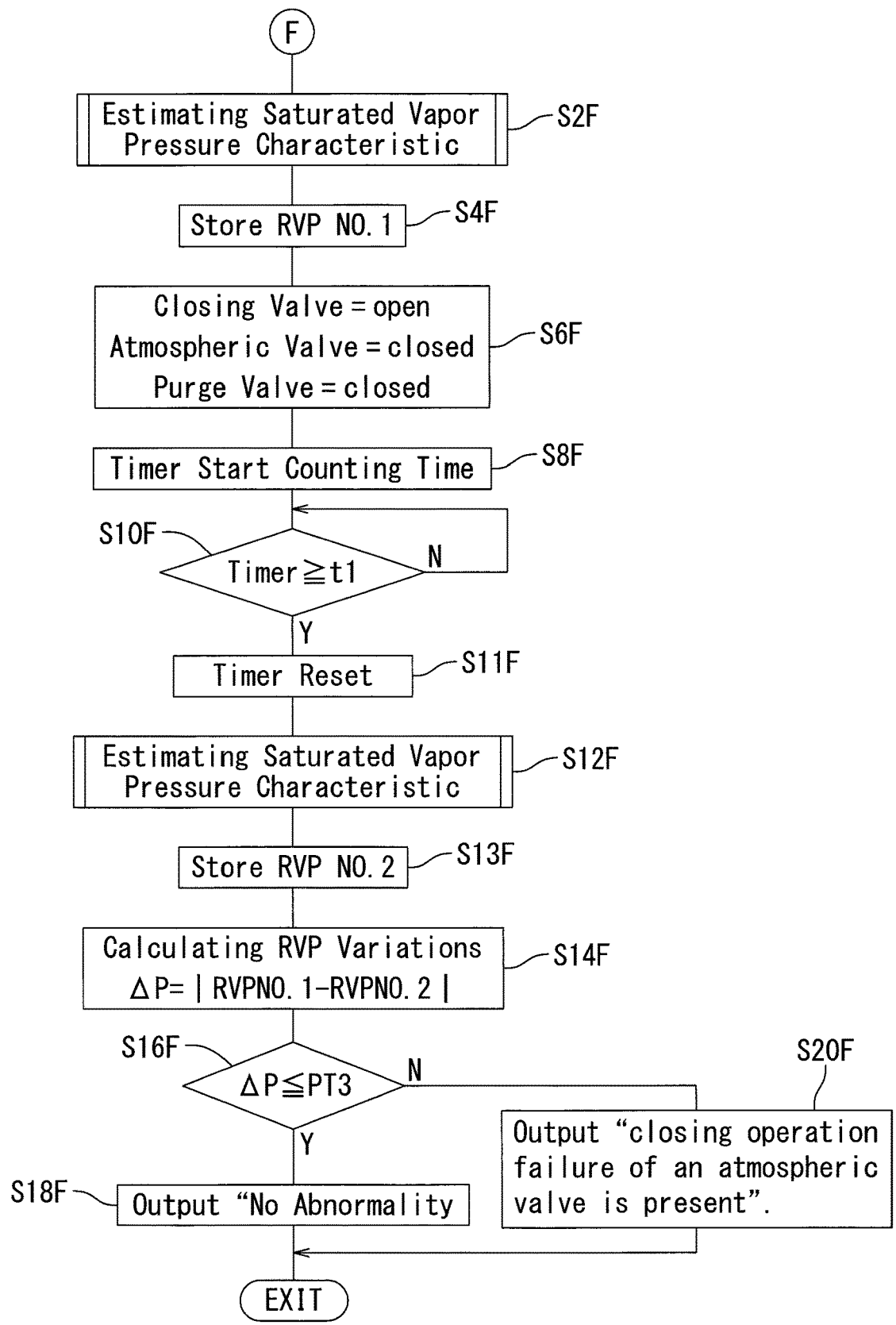
FIG. 9 is a flowchart illustrating a failure diagnosis program F for the system of FIG. 1.

FIG. 9 shows a program corresponding to a fifth failure diagnosis method or means for the above-described fuel vapor processing apparatus shown in FIG. 1. This program serves to determine whether or not there is a closing operation failure of the atmospheric valve 16. Hereinafter, the contents of this program will be described with reference to a region for time F in the time chart of FIG. 11.

When the program in FIG. 9 is executed, the saturated vapor pressure characteristics of the gas phase of the fuel in the fuel tank 2 at that moment will be estimated in Step S2F, similar to the way it was estimated in Step S2 of the program in FIG. 4. In Step S4F, the Reid vapor pressure (RVP) at a gas phase temperature of 37.8° C. is determined based on the estimated saturated vapor pressure characteristics and its value is stored as RVP NO. 1. In Step S6F, the closing valve 12 remains open, the atmospheric valve 16 is closed, and the purge valve 14 remains closed. Subsequently, in Step S8F to Step S13F, the Reid vapor pressure RVP NO. 2 is determined after a time t1 has elapsed and its value is stored. In Step S14F, the absolute value of the difference between RVP NO. 1 and RVP NO. 2 is determines as the RVP variation ΔP, in a similar as was done in Step S8 to Step S14 in FIG. 4.

In Step S16F of FIG. 9, it is determined whether or not the RVP variation ΔP is less than or equal to a third threshold value PT3. In Step S6F, the fuel in the fuel tank has stopped volatilizing since the purge valve 14 is closed, and the atmospheric valve 16 is closed. Therefore, the Reid vapor pressure should maintain essentially the same pressure after such a moment. However, if there is a failure such that the atmospheric valve 16 cannot be closed, and therefore stays open, the Reid vapor pressure lowers, as indicated by the broken line in the region for time F in FIG. 11. Therefore, Step S16F is determined to be negative, and the system output "closing operation failure of the atmospheric valve 16 is present" in Step S20F. The warning lamp 62 (see FIG. 2) is also illuminated. In contrast, if there is no closing operation failure of the atmospheric valve 16, the Reid vapor pressure will not be lowered, as indicated by the solid line in the region for time F in FIG. 11. Therefore, Step S16F is determined to be affirmative, and the system outputs "No abnormality" in Step S18F. Thereafter, the failure diagnosis process will end.

Figure 12:
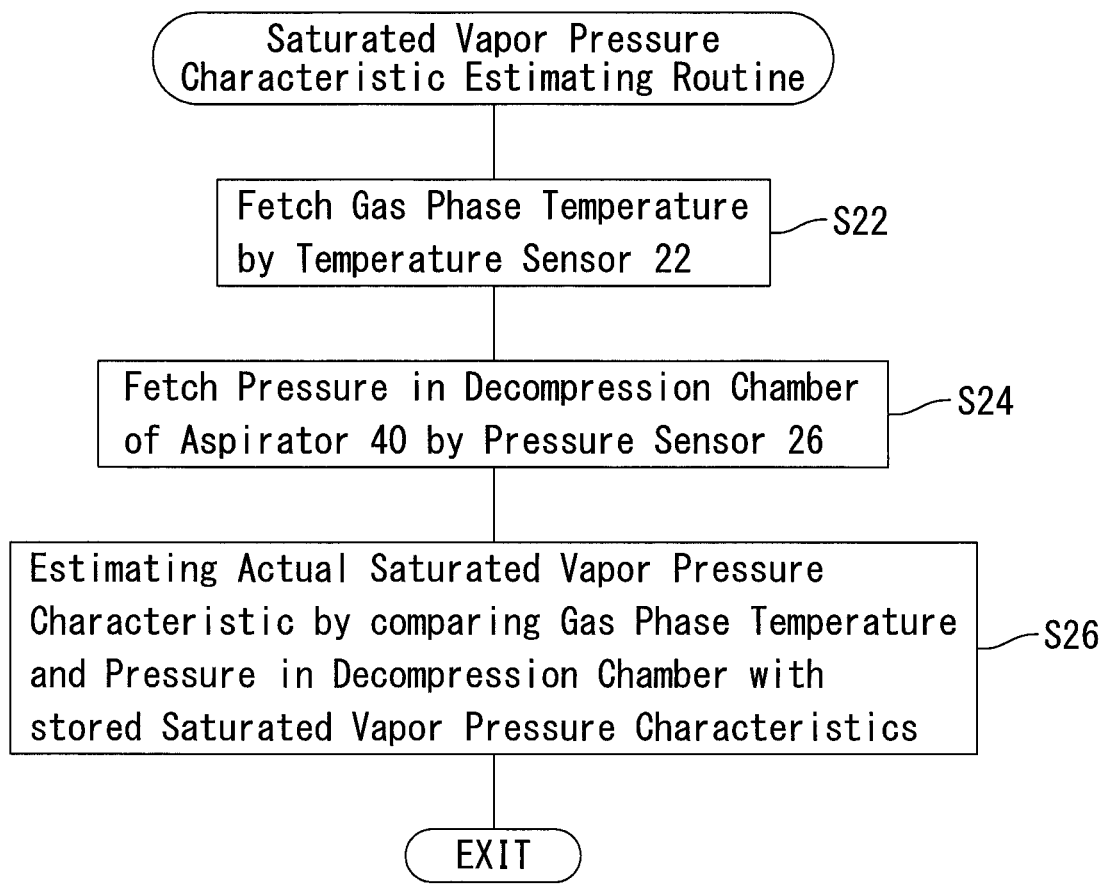
FIG. 12 is a flowchart illustrating a saturated vapor pressure characteristic estimating program for each of the failure diagnosis programs A-F.
Figure 13:
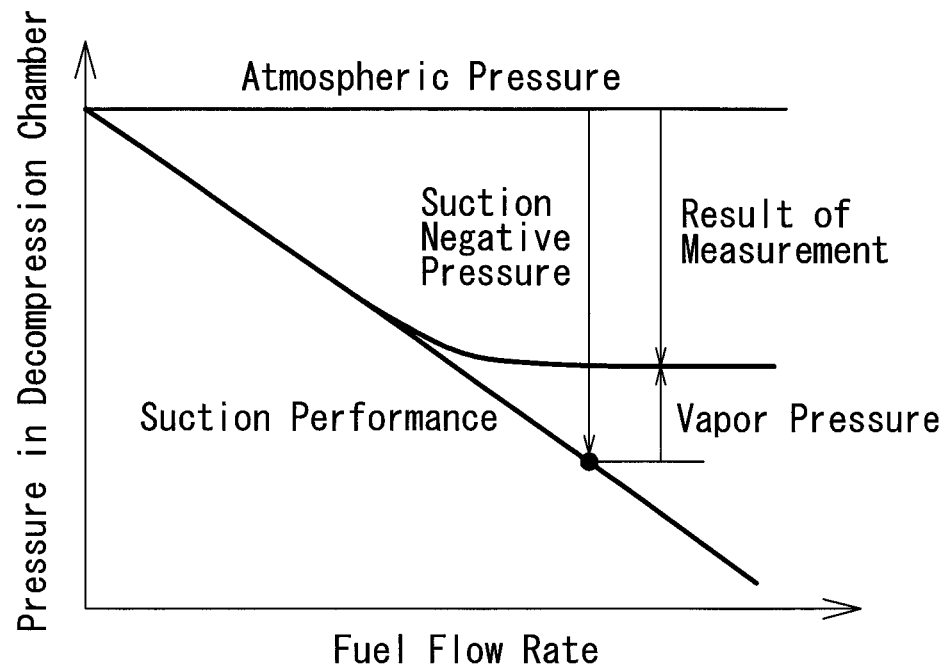
FIG. 13 is a characteristic diagram illustrating a change in pressure of a decompression chamber with respect to a fuel flow rate of the aspirator of FIG. 1.

FIG. 12 shows a first embodiment of a saturated vapor pressure characteristic estimating program, which can be used in Step S2 and Step S12 of FIG. 4. Hereinafter, the contents of this program will be described with reference to FIGS. 1 to 3 and FIGS. 12 to 14.

In Step S22 of FIG. 12, the temperature of the fuel in the gas phase within the fuel tank 2, as detected by the temperature sensor 22, is acquired. Further, in Step S24, the pressure of the decompression chamber 46 of the aspirator 40, as detected by the pressure sensor 26, is acquired. In a subsequent Step S26, the saturated vapor pressure characteristics of the fuel within the fuel tank 2 is estimated based on the gas phase temperature acquired in Step S22 and the pressure of the decompression chamber 46 acquired in Step S24.

Figure 14:
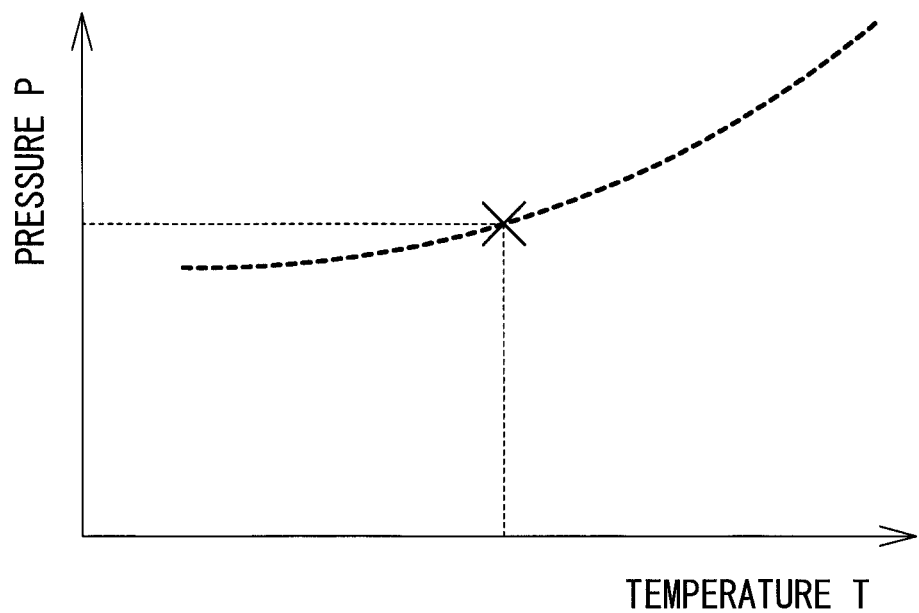
FIG. 14 is a characteristic diagram of the saturated vapor pressure for an estimation method of a saturated vapor pressure characteristic for the system of FIG. 1.

The fuel vapor is saturated in the decompression chamber 46 of the aspirator 40, shown in FIG. 3, when the operation of the aspirator 40 is stable. Therefore, the saturated vapor pressure (vapor pressure) can be determined based on the difference between the negative pressure of the decompression chamber 46 (suction negative pressure), which can be calculated based on the amount of fuel supplied from the fuel pump 8 to the aspirator 40, and the pressure actually detected by the pressure sensor 26 (result of measurement). To estimate the saturated vapor characteristics, a characteristic is identified. The characteristic may indicate how the vapor pressure corresponds to the temperature, as indicated by the broken line among a plurality of saturated vapor pressure characteristics that are stored in advance based on the temperature of the fuel in the gas phase within the fuel tank 2 and the vapor pressure as shown in FIG. 14. Here, instead of the temperature of the headspace in the fuel tank 2, the temperature within the decompression chamber 46 may be used.

Figure 15:
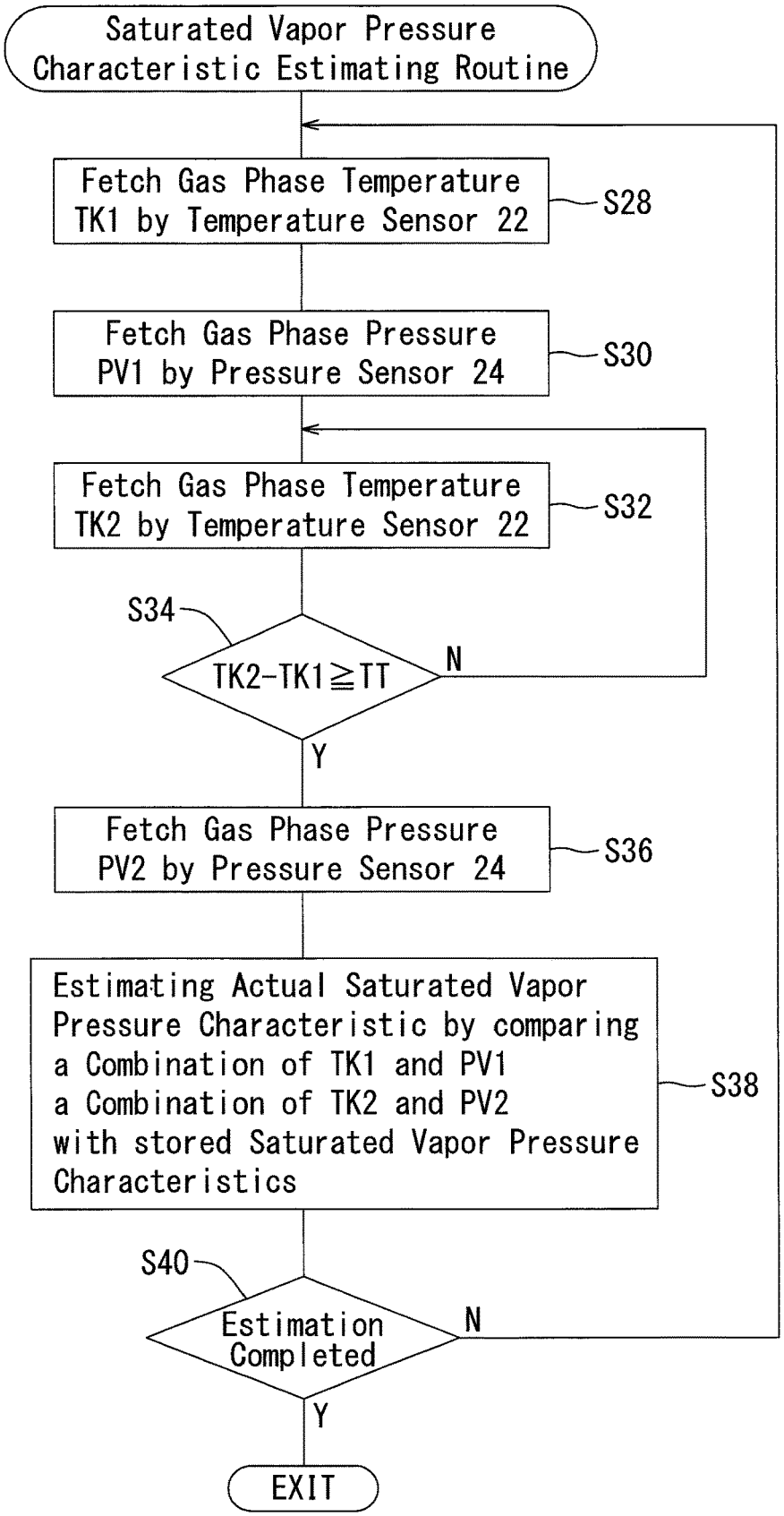
FIG. 15 is a flowchart illustrating a saturated vapor pressure characteristic estimating program according to a second embodiment.

FIG. 15 shows a second embodiment of a saturated vapor pressure characteristic estimating program, which can be used in Step S2 and Step S12 of FIG. 4. Hereinafter, the contents of this program will be described with reference to FIGS. 1, 2, and 15-17.

In Step S28 of FIG. 15, the temperature of the headspace within the fuel tank 2 detected by the temperature sensor 22 is acquired and stored as TK1. Also, in Step S30, the pressure of the headspace within the fuel tank 2 detected by the pressure sensor 24 is acquired and stored as PV1. In Step S32, the temperature of the headspace of the fuel tank 2 detected by the temperature sensor 22 is again acquired and stored as TK2. Further, in Step S34, it is determined whether the difference in temperature, TK2-TK1, has reached a preset temperature difference TT. If so, the process proceeds to Step S36. If not, the temperature of the headspace of the fuel tank 2 is again acquired and stored as TK2, In Step S36, the pressure of the headspace of the fuel tank 2 detected by the pressure sensor 24 at this time is acquired and stored as PV2. In the subsequent Step S38, a saturated vapor pressure characteristic is obtained, which corresponds to how the pressure detected by the pressure sensor 24 shifts from PV1 to PV2 in relation to how the temperature detected by the temperature sensor 22 varies from TK1 to TK2. If this characteristic is present among the saturated vapor pressure characteristics, which are stored in advance, this characteristic is estimated to be the saturated vapor pressure characteristic of the fuel in the fuel tank 2 at that moment. In Step S40, it is determined whether or not the estimation of the saturated vapor pressure characteristic, which was determined in Step S38, has been completed. The process of FIG. 15 repeats until it is determined that the estimation has been completed.

Figure 16:
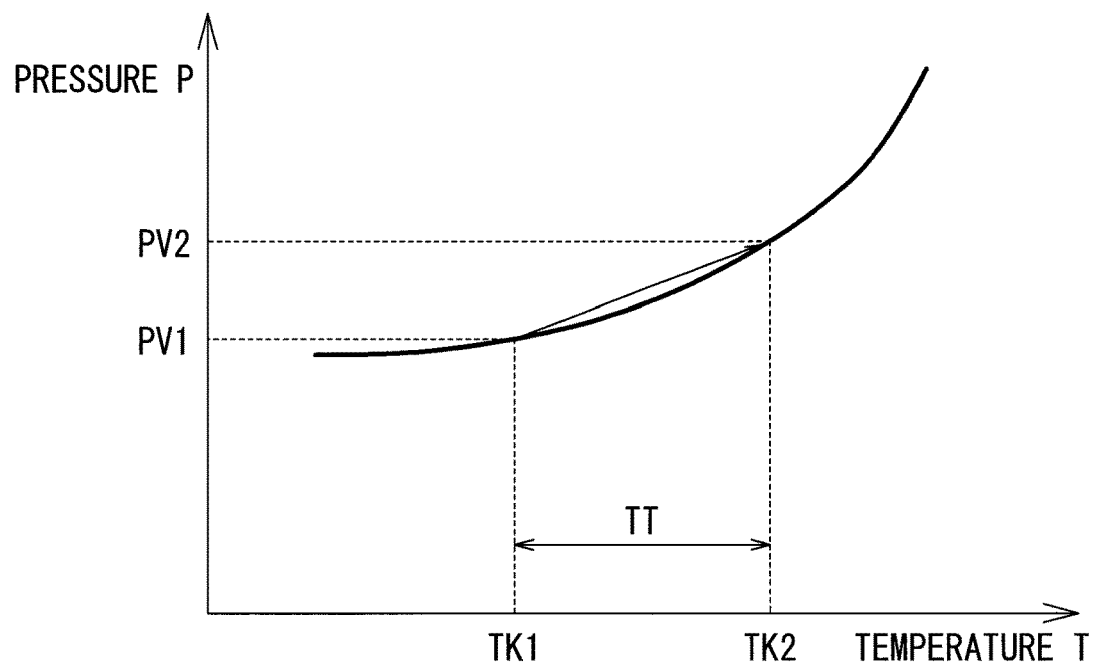
FIG. 16 is a diagram for a saturated vapor pressure characteristic for the saturated vapor pressure characteristic estimating program of FIG. 15.
Figure 17:
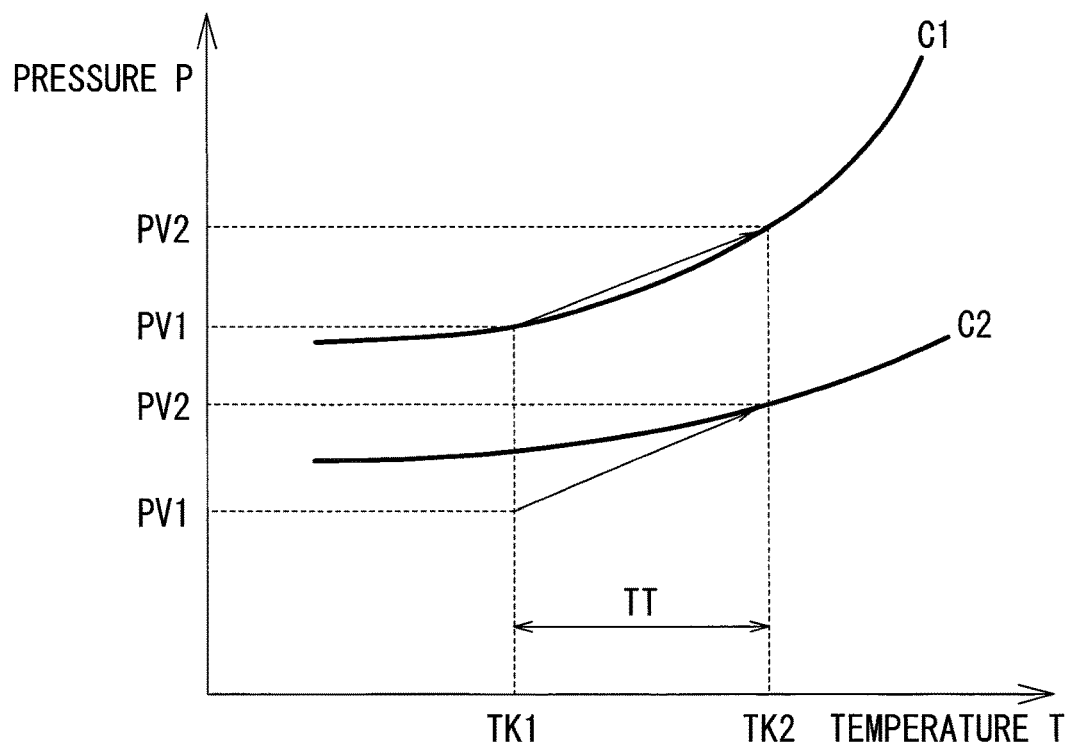
FIG. 17 is a diagram for two saturated vapor pressure characteristics for the saturated vapor pressure characteristic estimating program of FIG. 15.

FIG. 16 shows that a saturated vapor pressure characteristic is present and corresponds to the calculated gas phase pressure change (from PV1 to PV2) with respect, to the gas phase temperature change (from TK1 to TK2). Specifically, FIG. 16 shows the case where the estimation of the saturated vapor pressure characteristic of the fuel within the fuel tank 2 can be performed. In the example of FIG. 17, the measured gas phase pressure change (from the upper PV1 to the upper PV2) with respect to the gas phase temperature change (from TK1 to TK2) corresponds to a curve representing the saturated vapor pressure characteristic C1. Therefore, the saturated vapor pressure characteristic can be estimated as the curve corresponding to C1. On the other hand, when the measured gas phase pressure change (from the lower PV1 to the lower PV2) with respect to the gas phase temperature change (from T1 to T2) does not correspond, a curve representing a saturated vapor pressure characteristic such as the curve corresponding to C2, the saturated vapor pressure characteristic cannot be estimated at this moment.

According to the second embodiment, there is no need to detect the pressure of the decompression chamber 46 of the aspirator 40, which is in contrast to the first embodiment. Therefore, the aspirator 40 and the pressure sensor 26 can be omitted.

Figure 18:
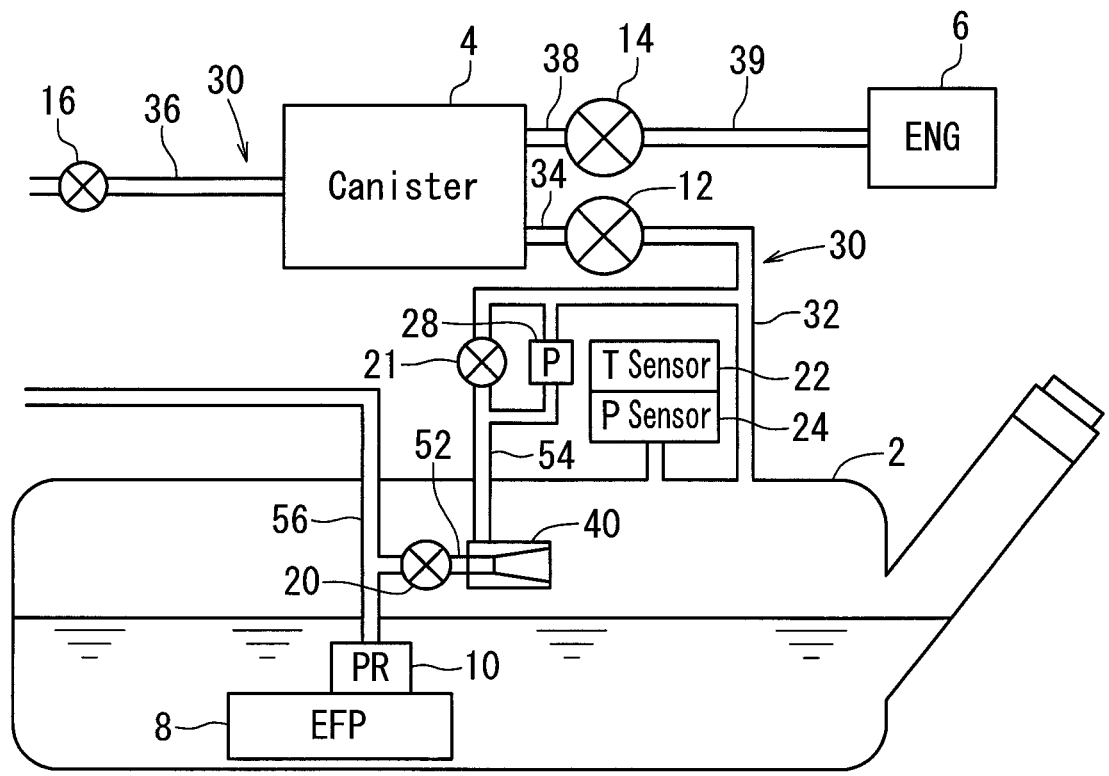
FIG. 18 is a schematic view of an embodiment of a system in accordance with the principles described herein.
Figure 20:
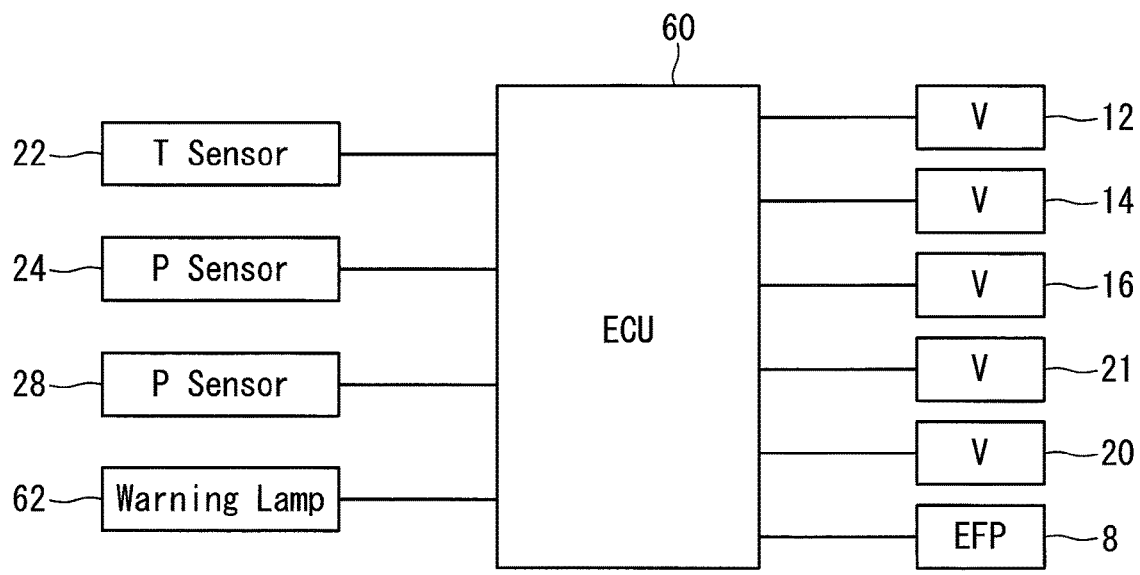
FIG. 20 is a block diagram of a control circuit for the system of FIG. 18.
Figure 21:
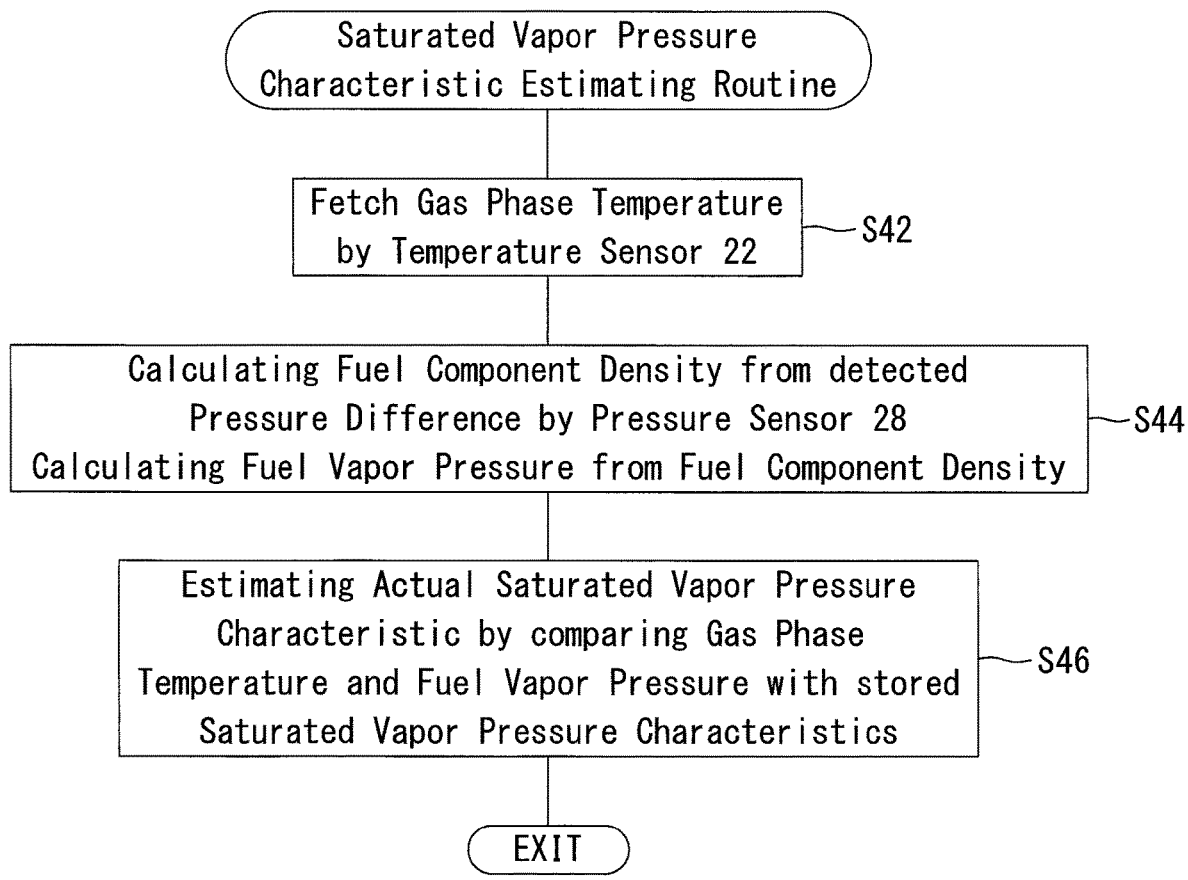
FIG. 21 is a flowchart illustrating a saturated vapor pressure characteristic estimating program for the system of FIG. 18.

FIGS. 18, 20, and 21 show a third embodiment of a saturated vapor pressure characteristic estimating program, which can be used in Step S2 and Step S12 of FIG. 4. FIGS. 18 and 20 show a system configuration of the third embodiment. Further, FIG. 21 shows the contents of the saturated vapor pressure characteristic estimating program of the third embodiment.

Figure 19:
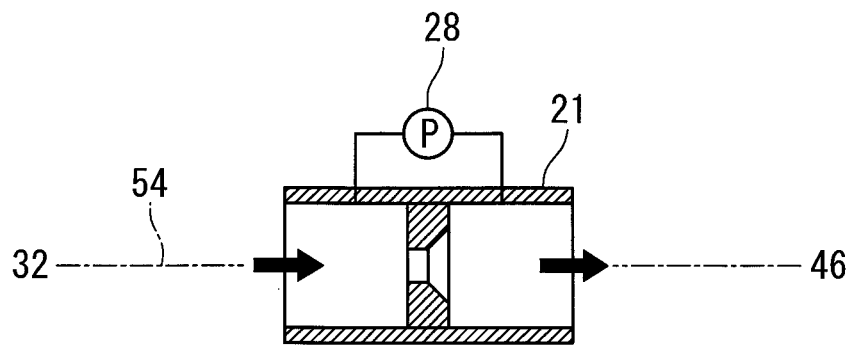
FIG. 19 is an enlarged view of the orifice valve of FIG. 18.

As shown in FIG. 1, a first end of the suction passage 54 according to the first embodiment is in fluid communication with the aspirator 40, and more specifically, the decompression chamber 46 of the aspirator 40. A second end of the suction passage 54 of the first embodiment is in fluid communication with the canister 4. On the other hand, as illustrated in FIG. 18, the second end of the suction passage 54 of the third embodiment is in fluid communication with the upstream vapor passage 32. Further, an orifice valve 21 is interposed in the suction passage 54. The orifice valve 21 can change to narrow the passage area for the fuel vapor flowing through the suction passage 54 as shown in FIG. 19. The fuel vapor flows through the orifice valve 21 from the upstream vapor passage 32 toward the decompression chamber 46 of the aspirator 40. The pressure sensor 28 is connected to the orifice valve 21. The pressure sensor 28 can detect the pressure difference between the upstream side and the downstream side of the orifice valve 21. As shown in FIG. 20, detected signals of the pressure sensor 28 can be acquired into a control unit 60. Further, signals from the control unit 60 may be used to change the passage area of the orifice valve 21. The system configuration of the third embodiment shown in FIG. 18 is essentially identical to that of the first embodiment, shown in FIG. 1 except that the structure of the suction passage 54 has been changed as described above.

FIG. 21 shows the third embodiment of the saturated vapor pressure characteristic estimating program, which can be used in Step S2 and Step 12 of FIG. 4. Hereinafter, the contents of this program will be described with reference to FIGS. 18 and 20-22.

The temperature of the headspace within the fuel tank 2 detected by the temperature sensor 22 is acquired in Step S42 of FIG. 21. In Step S44, the fuel component density is calculated from Bernoulli's equation based on the pressure difference of the orifice valve 21 detected by the pressure sensor 28, for instance by using the following equation:

$$\text{fuel component density} = \text{pressure difference}/(Q/CK)^2 \quad \text{(Equation 1)}$$

where, Q: flow rate through orifice valve 21, C: flow rate coefficient, K: cross-section coefficient.

Figure 22:
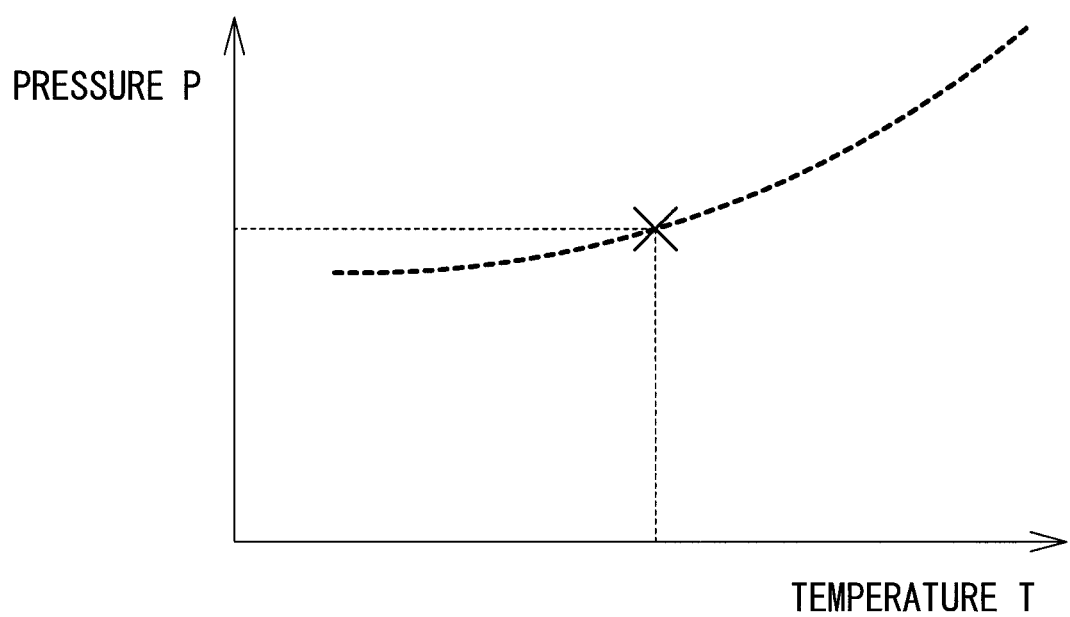
FIG. 22 is a diagram for the saturated vapor pressure characteristic for the saturated vapor pressure characteristic estimating program of FIG. 21.

Further, in Step S44, the fuel vapor pressure, which correlates with the fuel component density determined as described above, is calculated from the fuel component density. In the following Step S46, the saturated vapor pressure characteristic is estimated based on the headspace temperature detected by the temperature sensor 22 and the calculated fuel vapor pressure. This estimation may be done by comparing these values with the saturated vapor pressure characteristics that are store in advance. FIG. 22 shows the estimation of the saturated vapor pressure characteristic indicated by a broken line, the estimation being based on the headspace temperature and the fuel vapor pressure.

In each of the above embodiments, each of the processes for the saturated vapor pressure characteristic estimating routine of Steps S2, S12, S2B, S12B, S2C, S12C, S2D, S12D, S2E, S12E, S2F, S12F, and FIG. 12; the saturated vapor pressure characteristic estimating routine of FIG. 15; and the saturated vapor pressure characteristic estimating routine of FIG. 21 is an embodiment of a saturated vapor pressure characteristic estimating method or means. Further, each of the processes for the failure diagnosis routines of FIG. 4 to FIG. 9 is an embodiment of a failure diagnosis method or means. Each of the processes in Steps S22, S28. S32, and S42 is an embodiment of the headspace temperature detecting method or means. Each of the processes of Steps S30 and S36 is an embodiment of a vapor pressure detecting method or means. The process in Step S44 is an embodiment of a density detecting method or means. Further, each of the processes for the failure diagnosis routines in FIGS. 4 and 7 are an embodiment of a first failure diagnosis method or means. Each of the processes of the failure diagnosis routine of FIG. 5 is an embodiment of a second failure diagnosis method or means. Each of the processes for the failure diagnosis routine in FIG. 8 is an embodiment of a third failure diagnosis method or means. Each of the processes for the failure diagnosis routine of FIG. 6 is an embodiment of a fourth failure diagnosis method or means. Each of the processes for the failure diagnosis routine of FIG. 9 is an embodiment of a fifth failure diagnosis method or means.

Although the technology disclosed herein has been described above in terms of specific embodiments, it may be implemented in various other forms. For example, in the above embodiments, the specific temperature to read the saturated vapor pressure from the saturated vapor pressure characteristic is determined as the Reid vapor pressure (RVP) at a gas phase temperature of 37.8° C. Alternatively, the specific temperature may be any other temperature. In the above embodiments, the blockage failure in the vapor passage and the atmospheric passage is diagnosed without distinction. Alternatively, each blockage failure may be diagnosed with distinction. In the above embodiment, the headspace temperature is directly detected by the temperature sensor 22. Alternatively, for example, fuel temperature or engine coolant temperature may also be used. Further, the headspace temperature may be determined by using the fuel temperature, ambient air temperature, and a residual fuel amount within the fuel tank.

In the above embodiments, the density detecting means is a gas density meter, which may include, for example, a pressure sensor 28 and an orifice valve 21, an embodiment of which is shown in FIG. 18. Alternatively, the density detecting means may be an oscillation-type gas density meter to detect gas density by measuring resonance frequencies, or any other suitable device.

The control unit 60 may include at least one programmed electronic processor. The control unit 60 may include at least one memory configured to store instructions or software to be executed by the electronic processor to carry out at least one of the functions of the control unit 60 described herein. For example, in some embodiments, the control unit 60 may be implemented as a microprocessor with a separate memory, or any other suitable device.

The control unit 60 may include a volatile and/or a non-volatile memory. Examples of suitable control unit 60 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof.

Where the term "processor" or "central processing unit" or "CPU" is used for identifying a unit performing specific functions, it should be understood that, unless otherwise explicitly stated, those functions can be carried out by a single processor or multiple processors arranged in any form, including parallel processors, serial processors, tandem processors, or cloud processing/cloud computing configurations. The software may include, for example, firmware, one or more applications, program data, filters, rules, one or more program modules, and/or other executable instructions.

The various examples described in detail above, with reference to the attached drawings, are intended to be representative of the present disclosure, and are thus non-limiting embodiments. The detailed description is intended to teach a person of skill in the art to make, use, and/or practice various aspects of the present teachings, and thus does not limit the scope of the disclosure in any manner. Furthermore, each of the additional features and teachings disclosed above may be applied and/or used separately or with other features and teachings in any combination thereof, so as to provide an improved failure diagnostic device for a fuel vapor processing apparatus, and/or methods of making and using the same.

What is claimed is:

1. A failure diagnostic device for a fuel vapor processing apparatus, the device comprising:
    a canister;
    a vapor passage coupling the canister to a fuel tank;
    a vapor valve provided along the vapor passage and configured to open and close the vapor passage;
    a purge passage extending from the canister;
    a purge valve provided along the purge passage and configured to open and close the purge passage;
    an atmospheric passage connected to the canister and configured to supply atmospheric air into the canister;
    an atmospheric valve provided along the atmospheric passage and configured to open and close the atmospheric passage; and
    a control unit implemented by at least one programmed processor,
    wherein the control unit is configured:
        to determine a plurality of saturated vapor pressure characteristics within the fuel tank over a period of time,
        to determine a saturated vapor pressure for each of the plurality of saturated vapor pressure characteristics,
        to diagnose whether or not (i) a leakage failure of the fuel vapor processing apparatus or (ii) a blockage failure of the fuel vapor processing apparatus is present based on a change in the determined saturated vapor pressures over the period of time under a condition in which all of the vapor valve, purge valve, and atmospheric valve are closed or under a condition in which at least one of the vapor valve, purge valve, and atmospheric valve are open, and
    wherein the diagnosis of the leakage failure or the blockage failure is based on the change in the saturated vapor pressures at a specific temperature over the period of time.

2. The failure diagnostic device of claim 1, further comprising:
    a gas phase temperature sensor configured to detect a temperature of a headspace in the fuel tank; and
    an aspirator including:
        a narrow flow passage section having a passage cross-sectional area narrower than that of an upstream side, and
        a decompression chamber positioned on the upstream side of the narrow flow passage, and
    wherein the aspirator is configured to generate a negative pressure in the decompression chamber due to a Venturi effect;
    wherein the control unit is configured to determine the saturated vapor pressure by comparing a fuel vapor pressure determined based on a pressure of the decompression chamber of the aspirator and on a temperature detected by the gas phase temperature sensor with a stored saturated vapor pressure characteristic for that temperature.

3. The failure diagnostic device of claim 1, further comprising:
    a gas phase temperature sensor configured to detect a temperature representing a temperature of a headspace within the fuel tank; and
    a vapor pressure sensor configured to detect a vapor pressure of a fuel vapor in the headspace within the fuel tank;
    wherein, after the temperature detected by the gas phase temperature sensor changes, the control unit is further configured to estimate the saturated vapor pressure by comparing a plurality of vapor pressures detected by the vapor pressure sensor with a plurality of stored saturated vapor pressure characteristics at each of the same temperatures as detected by the gas phase temperature detecting sensor.

4. The failure diagnostic device of claim 1, further comprising:

a gas phase temperature sensor configured to detect a temperature representing a temperature of a headspace in the fuel tank; and a density detector configured to determine a density of a fuel component of the fuel vapor in the headspace of the fuel tank;

wherein the control unit is further configured to estimate the saturated vapor pressure by comparing a fuel vapor pressure determined in accordance with the density of the fuel component as determined by the density detector and the temperature detected by the gas phase temperature sensor with a stored saturated vapor pressure characteristic of fuel at the same temperatures as detected by the gas phase temperature detecting sensor.

5. The failure diagnostic device of claim 1, wherein, in accordance with the change in the saturated vapor pressure in a headspace within the fuel tank over time and while the vapor passage is instructed to be closed and while the purge valve is closed, the diagnosis of the control unit includes determining whether or not a leakage failure is present in at least one of the fuel tank or a portion of the vapor passage between the fuel tank and the vapor valve.

6. The failure diagnostic device of claim 5, wherein, based on the change in a saturated vapor pressure in the headspace within the fuel tank over time when the vapor valve is instructed to be opened, the atmospheric valve is closed, and the purge valve is closed, and after the control unit has diagnosed the absence of the leakage failure of the fuel tank and the portion of the vapor passage between the fuel tank and the vapor valve, the diagnosis of the control unit includes determining:

whether or not a leakage is present in at least any one of the canister, a portion of the vapor passage between the canister and the vapor valve, a portion of the atmospheric passage between the canister and the atmospheric valve, or a portion of the purge passage between the canister and the purge valve, whether or not a blockage failure is present in a portion of the vapor passage including the vapor valve, and/or whether or not an opening operation failure of the vapor valve is present.

7. The failure diagnostic device of claim 5, wherein, in accordance with a change in the saturated vapor pressure in the headspace within the fuel tank over time while the vapor valve is instructed to be opened, the atmospheric valve is open, and the purge valve is closed, and after the control unit has diagnosed the absence of the leakage failure of the fuel tank and the portion of the vapor passage between the fuel tank and the vapor valve, the diagnosis of the control unit includes determining:

whether or not a blockage failure is present in the vapor passage including the vapor valve, and whether or not an opening operation failure of the vapor valve is present.

8. The failure diagnostic device of claim 6, wherein, in accordance with a change in the saturated vapor pressure in the headspace of the fuel tank over time while the vapor valve is open, the atmospheric valve is instructed to be opened, the purge valve is closed, and after the control unit has diagnosed the absence of the blockage failure of the vapor passage including the vapor valve and/or the absence of the opening operation failure of the vapor valve, the diagnosis of the control includes determining:

whether or not a blockage failure is present in the atmospheric passage including the atmospheric valve, and/or whether or not an opening operation failure of the atmospheric valve is present.

9. The failure diagnostic device of claim 7, wherein, in accordance with a change in the saturated vapor pressure in the headspace within the fuel tank over time while the atmospheric valve is instructed to be closed and while the purge valve is closed, and after the control unit has diagnosed the absence of the blockage failure of in the vapor passage including the vapor valve, and/or the opening operation failure of the vapor valve, the diagnosis of the control unit includes determining:

whether or not a closing operation failure of the atmospheric valve is present.

* * * * *